US009999557B2

(12) United States Patent
Diaz-Flores et al.

(10) Patent No.: US 9,999,557 B2
(45) Date of Patent: Jun. 19, 2018

(54) ROBOTIC MOBILITY DEVICE

(71) Applicant: Challenging Solutions, Inc., El Cerrito, CA (US)

(72) Inventors: Ernesto Diaz-Flores, El Cerrito, CA (US); Wesley Siebenthal, Orcutt, CA (US)

(73) Assignee: CHALLENGING SOLUTIONS, INC., El Cerrito, CA (US)

( * ) Notice: Subject to any disclaimer, the term of this patent is extended or adjusted under 35 U.S.C. 154(b) by 0 days. days.

(21) Appl. No.: 15/210,598

(22) Filed: Jul. 14, 2016

(65) Prior Publication Data
US 2018/0014988 A1    Jan. 18, 2018

(51) Int. Cl.
| A61G 5/10 | (2006.01) |
| A61G 5/00 | (2006.01) |
| A61G 5/04 | (2013.01) |
| A61G 5/02 | (2006.01) |

(52) U.S. Cl.
CPC .......... *A61G 5/1059* (2013.01); *A61G 5/006* (2013.01); *A61G 5/025* (2013.01); *A61G 5/04* (2013.01)

(58) Field of Classification Search
CPC ...... A61G 5/1059; A61G 5/006; A61G 5/025; A61G 5/04
See application file for complete search history.

(56) References Cited

U.S. PATENT DOCUMENTS

| 6,068,280 A * | 5/2000 | Torres ..................... A61G 5/045 180/328 |
| 6,176,335 B1 * | 1/2001 | Schaffner ............... A61G 5/043 180/65.1 |
| 6,357,776 B1 * | 3/2002 | Goertzen ................. A61G 5/00 180/907 |
| 6,715,784 B2 * | 4/2004 | Koerlin .................. A61G 5/006 280/304.1 |
| 6,976,699 B2 * | 12/2005 | Koerlin .................. A61G 5/006 280/304.1 |
| 7,348,747 B1 * | 3/2008 | Theobold ................. B25J 5/005 318/568.11 |
| 7,516,984 B2 * | 4/2009 | Tang ...................... A61G 5/043 180/65.1 |

(Continued)

FOREIGN PATENT DOCUMENTS

| JP | 2005348761 A | * 12/2005 |
| JP | 2007143859 A | * 6/2007 |

OTHER PUBLICATIONS

International Search Report and Written Opinion from PCT Application No. PCT/US16/46190 dated Oct. 13, 2016, 13 pages.

*Primary Examiner* — Tuan C To
(74) *Attorney, Agent, or Firm* — Stoel Rives LLP

(57) ABSTRACT

A mobility device, including a base, a first omnidirectional wheel mounted at a first side of a forward portion of the base to rotate about a first axis, a second omnidirectional wheel mounted at a second side of the forward portion of the base to rotate about the first axis, a third wheel mounted at a rearward portion of the base to rotate about a second axis, a drive system to move the first omnidirectional wheel, the second omnidirectional wheel, and the third wheel according to input received indicating a desired motion of the mobility device, a seat for a user of the mobility device, and a linear actuator coupling the seat to the base to drive the adjustable seat in a vertical direction according to the input received indicating the desired motion of the mobility device.

18 Claims, 25 Drawing Sheets

(56) References Cited

U.S. PATENT DOCUMENTS

| | | | |
|---|---|---|---|
| 7,614,699 B2* | 11/2009 | Torres | A61G 5/045 |
| | | | 297/344.14 |
| 8,474,848 B2* | 7/2013 | Bernatsky | A61G 5/1062 |
| | | | 280/250.1 |
| 9,073,399 B1* | 7/2015 | Richter | B60G 17/0165 |
| 2003/0205883 A1 | 11/2003 | Bergstrom et al. | |
| 2004/0051279 A1* | 3/2004 | Grant | A61G 5/1059 |
| | | | 280/638 |
| 2004/0094944 A1* | 5/2004 | Goertzen | A61G 5/043 |
| | | | 280/755 |
| 2005/0046129 A1* | 3/2005 | Antonishak | A61G 5/043 |
| | | | 280/47.4 |
| 2007/0084648 A1* | 4/2007 | DuFresne | A61G 5/1059 |
| | | | 180/65.1 |
| 2007/0108721 A1 | 5/2007 | Bayne et al. | |
| 2007/0152427 A1* | 7/2007 | Olsen | A61G 5/046 |
| | | | 280/649 |
| 2007/0227787 A1 | 10/2007 | Kuramoto | |
| 2010/0155156 A1* | 6/2010 | Finkelstein | B25J 5/007 |
| | | | 180/54.1 |
| 2011/0040427 A1* | 2/2011 | Ben-Tzvi | B25J 5/005 |
| | | | 701/2 |
| 2012/0221146 A1* | 8/2012 | Zhang | B25J 9/0078 |
| | | | 700/260 |
| 2013/0008732 A1* | 1/2013 | Richter | A61G 5/04 |
| | | | 180/167 |
| 2013/0231779 A1* | 9/2013 | Purkayastha | B25J 9/1697 |
| | | | 700/259 |
| 2014/0142755 A1* | 5/2014 | Iruma | B25J 9/1612 |
| | | | 700/247 |
| 2014/0232174 A1 | 8/2014 | Zdrahal et al. | |
| 2014/0262575 A1* | 9/2014 | Richter | A61G 5/047 |
| | | | 180/167 |
| 2015/0137474 A1 | 5/2015 | Peek | |
| 2016/0101664 A1* | 4/2016 | Richter | B60G 99/002 |
| | | | 701/49 |

* cited by examiner

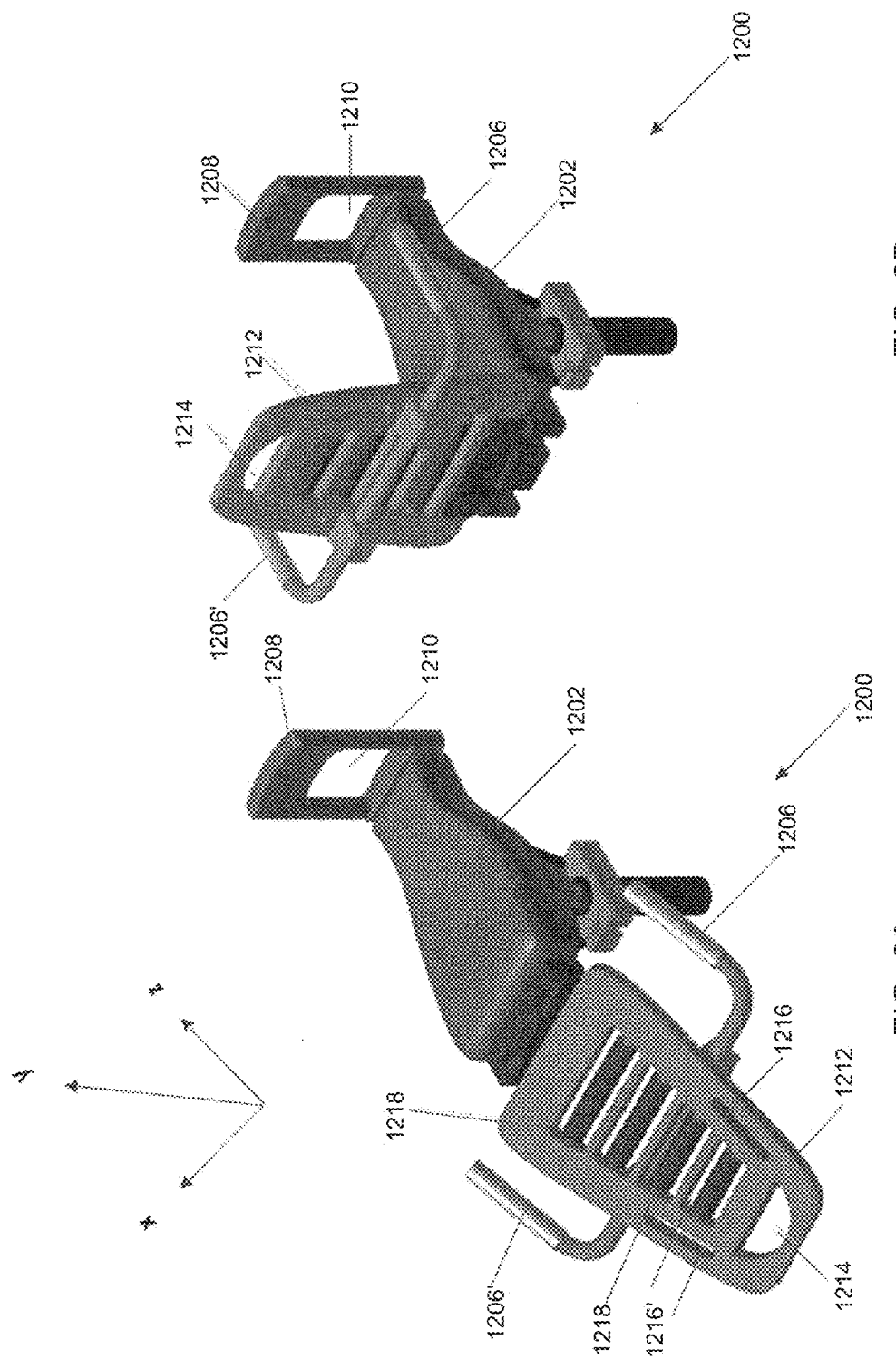

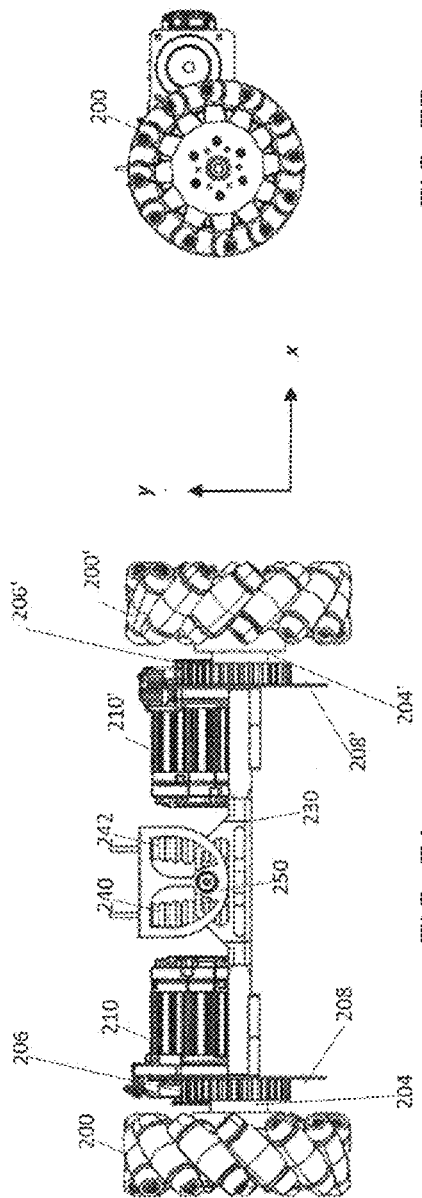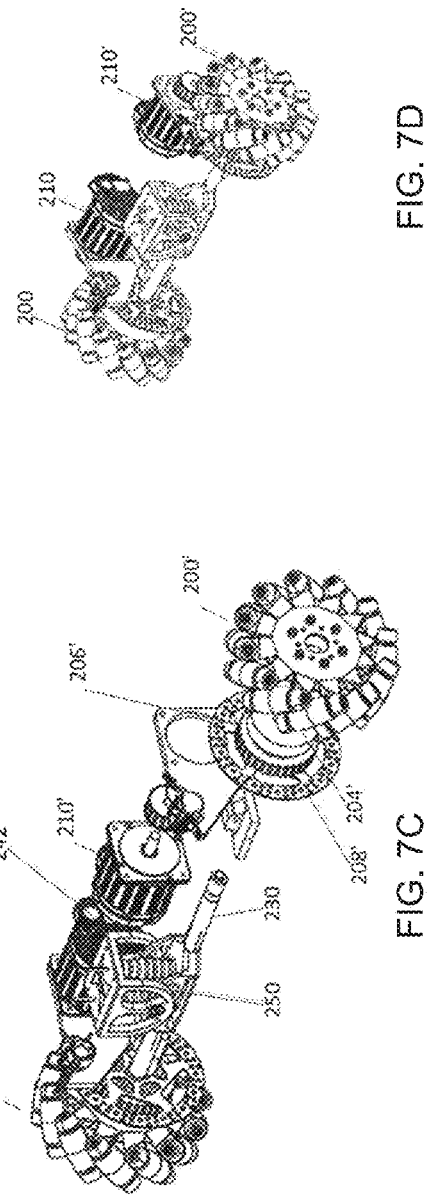

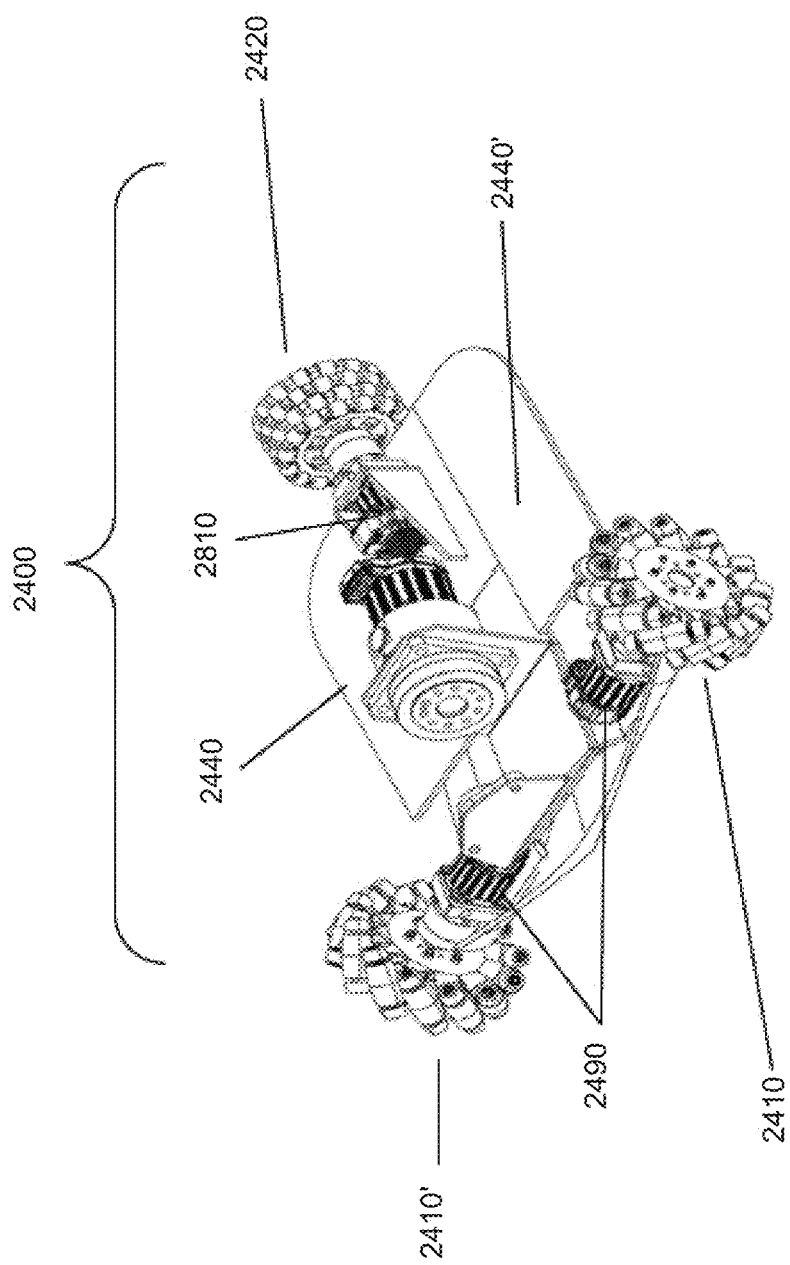

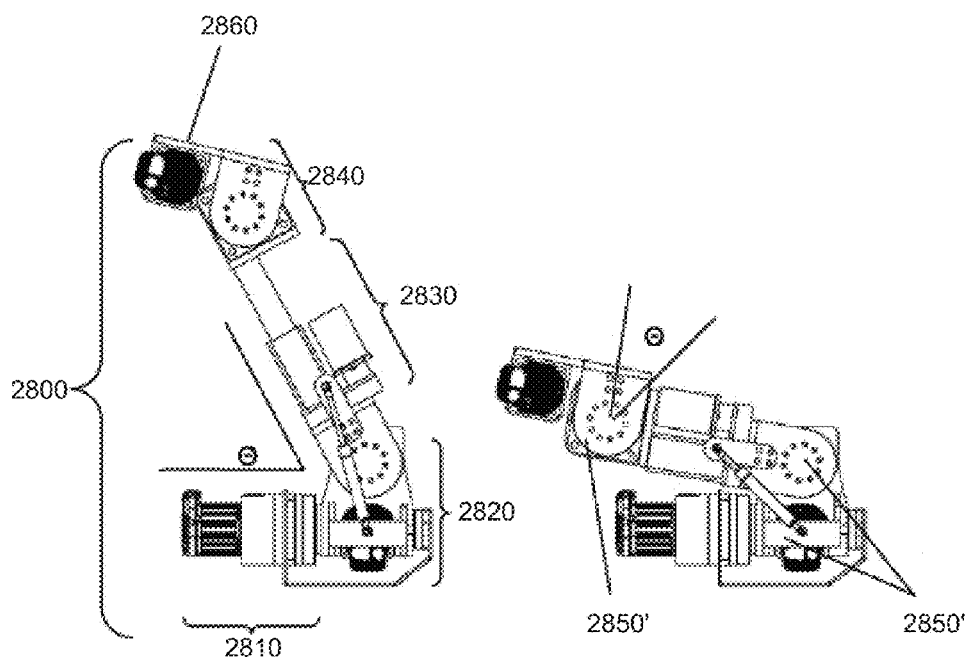
FIG.12A  FIG.12B
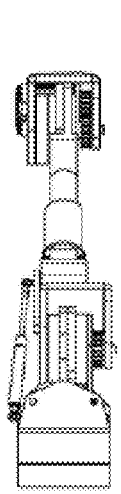 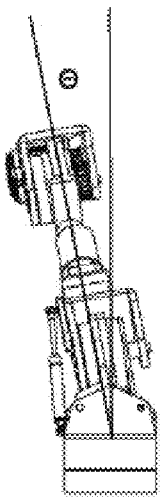
FIG.12C  FIG.12D

ROBOTIC MOBILITY DEVICE

TECHNICAL FIELD

This disclosure relates to a mobility device, and more particularly, to an omnidirectional and balance controlled mobility device.

BACKGROUND

Over 250,000 people in the U.S. have spinal cord injuries and there are approximately 11,000 new injuries per year. Persons with spinal cord injuries face many challenges that could be reduced with the appropriate equipment and resources. For example, passive standing is widely used clinically in both acute and chronic spinal cord injury (SCI) care. Further, people bound to wheelchairs need exercise. At a minimum, passive standing provides the patient with psychological benefits (such as being eye to eye with peers, not being looked down upon, having higher accessibility, freedom to operate in environments adapted for standing people, etc.), but it may also provide physiological benefits in preventing soft tissue contractures, bone loss, muscle atrophy, blood circulation, fatigue, digestion and excretion issues, etc.

Additionally, there are over 12 million Americans with different mobility limitations due to stroke, cerebral palsy, multiple sclerosis, muscular dystrophy, ALS, traumatic brain injury, etc., most of whom require mobility assistance.

Currently available mobility devices do not address the many and varied needs of persons with mobility limitations.

Moreover, persons bound to wheelchairs face injuries and other morbidities associated to their use of wheelchairs. Manual wheelchairs, for example, lead to shoulder, elbow, and wrist repetitive strain injuries while powered wheelchairs lead to obesity and diabetes. Both wheelchair types are also associated with blood circulation problems, as well as digestion and urinary problems and pressure sores among others.

In addition to people permanently bound to wheelchairs, there are over 15 million people in the U.S., largely among the elderly population, with mobility impairments and limitations. Such population faces a decrease in autonomy and independence due to their reduced mobility and accessibility, and a general negative impact on their well being and lifestyle.

Another population segment that sees a negative impact in their health due to constraints in mobility are people who, due to their work or responsibilities, are required to spend a lot of time in either sitting or standing positions. The number of people in such situations are hard to quantify as there are no comprehensive studies done on this regard, but those numbers may over exceed the tens of millions of people only in the U.S. An example of such populations include assembly line workers, surgeons and other personnel in operating rooms, clerks, administrative assistants, security staff, museum workers, etc.

For all of the above outlined populations, improved mobility devices may be desirable and beneficial. Improved mobility devices may be further desriable that provide transitioning from sitting to a full standing position with a natural, ergonomic and physiological way; rehabilitation with a gradual sit-stand transition; omni-directionality that allows movement and transportation in any direction and rotations; hybrid drive/propulsion with both human powered and battery powered capabilities to provide the benefits of both modes while reducing injuries and morbidities associated with the use of only manual or only powered mobility devices; compact design that favors greater accessibility, mainly through narrow spaces, which can include three wheel structures; an adapting and morphing seat that adjusts to the user's body and needs with the capacity for orbital movement; suspension systems that absorb the impact of riding over uneven surfaces, and intelligence from a computer interface that can control the device with both hands-on and hands-off systems, and that can integrate any assistive technology, connectivity, sensors, communications and alert systems.

SUMMARY

Embodiments of the disclosure relate to a mobility device comprising a seat system, a control system, and a base system. Some embodiments further include a robotic elevation system to raise the mobility device from a seated position to a standing position. The control system may be a manual and/or an electronic control system. In some embodiments, the base system includes an omnidirectional drive system.

Additional aspects and advantages will be apparent from the following detailed description of preferred embodiments, which proceeds with reference to the accompanying drawings.

BRIEF DESCRIPTION OF THE DRAWINGS

FIGS. 6A-6E are perspective views of a seat system of a mobility device according to some embodiments of the disclosed technology.

FIGS. 7A-7E are perspective views of a drive system of a mobility device according to some embodiments of the disclosed technology.

FIGS. 11A-11B are perspective views of a base system according to some embodiments of the disclosed technology.

FIGS. 12A-12D are perspective views of a robotic elevation system according to some embodiments of the disclosed technology.

DETAILED DESCRIPTION OF PREFERRED EMBODIMENTS

Figure 1:
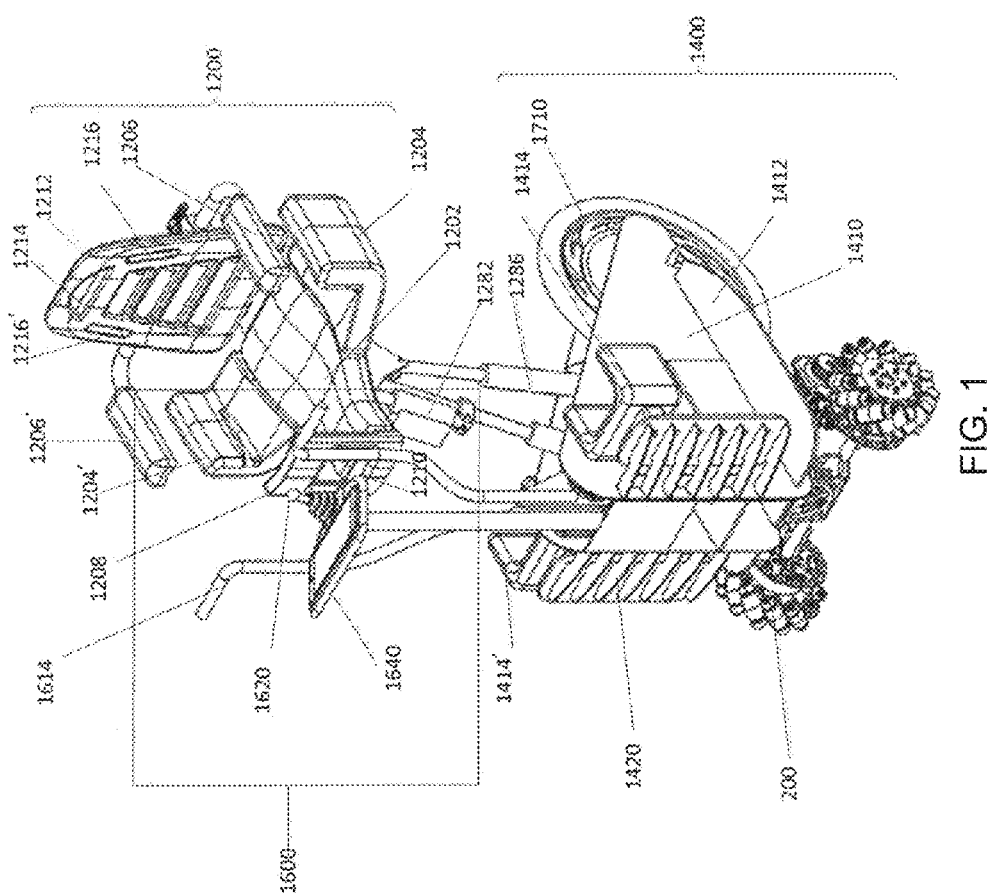
FIG. 1 illustrates one embodiment of a mobility device of the disclosed technology.

FIG. 1 is a perspective view of a mobility device according to some embodiments. The mobility device in these embodiments generally has a seat system 1200, a base system 1400, and a control system 1600.

The seat system 1200 is discussed in further detail below with respect to FIGS. 6A-6F. However, as shown generally in FIG. 1, the seat system 1200 has a main seating body 1202 which is a horizontal portion that can be flat or conformable to a user's buttocks. On one or both sides of the main seating body 1202 are seat wings 1204, 1204' which are connectable to the main seating body. One or more side arms 1206,1206' can also be provided. A frontal arch 1208 is provided which is connectable to a first end of the main seat body 1202. A back support 1212 is also provided, as discussed in further detail below. The back support 1212 has one or more apertures 1214, 1216, 1216' which enable gripping of the back support for when a user is entering or exiting the mobile device.

In some embodiments, the controller system 1600 has two handle bars 1610, 1612 with handles 1614, 1616. The control system 1600 also may include an electronic controller 1620, such as the joystick shown in FIG. 1 and/or a computer interface or console 1640 to allow the user to control all the functions of the device as well as provide additional connectivity for the user with internet, phone, and social media. The computer interface 1640 may include a mount for a personal electronic device, such as a tablet or mobile phone.

Figure 2:
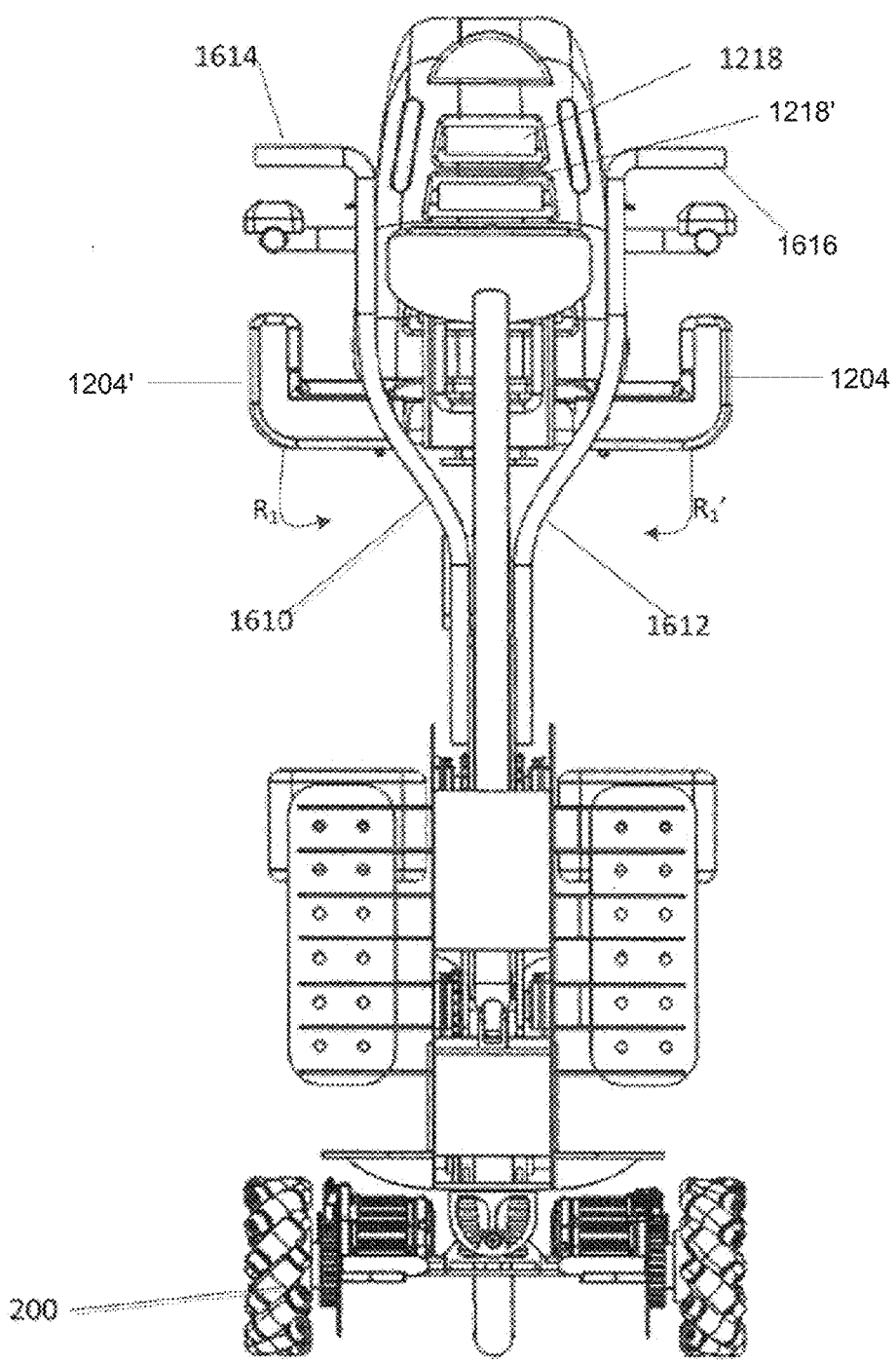
FIG. 2 illustrates a front view of the mobility device of FIG. 1.

FIG. 2 illustrates a front view of the mobility device of FIG. 1. As can be seen in FIG. 2, the seat wings 1204, 1204' are rotatable in the direction of R1 so that the seat wings 1204, 1204' are capable of rotating away from the plane formed by the main seating body 1202, to allow a user to easily enter or exit the mobility device.

Figure 3A:
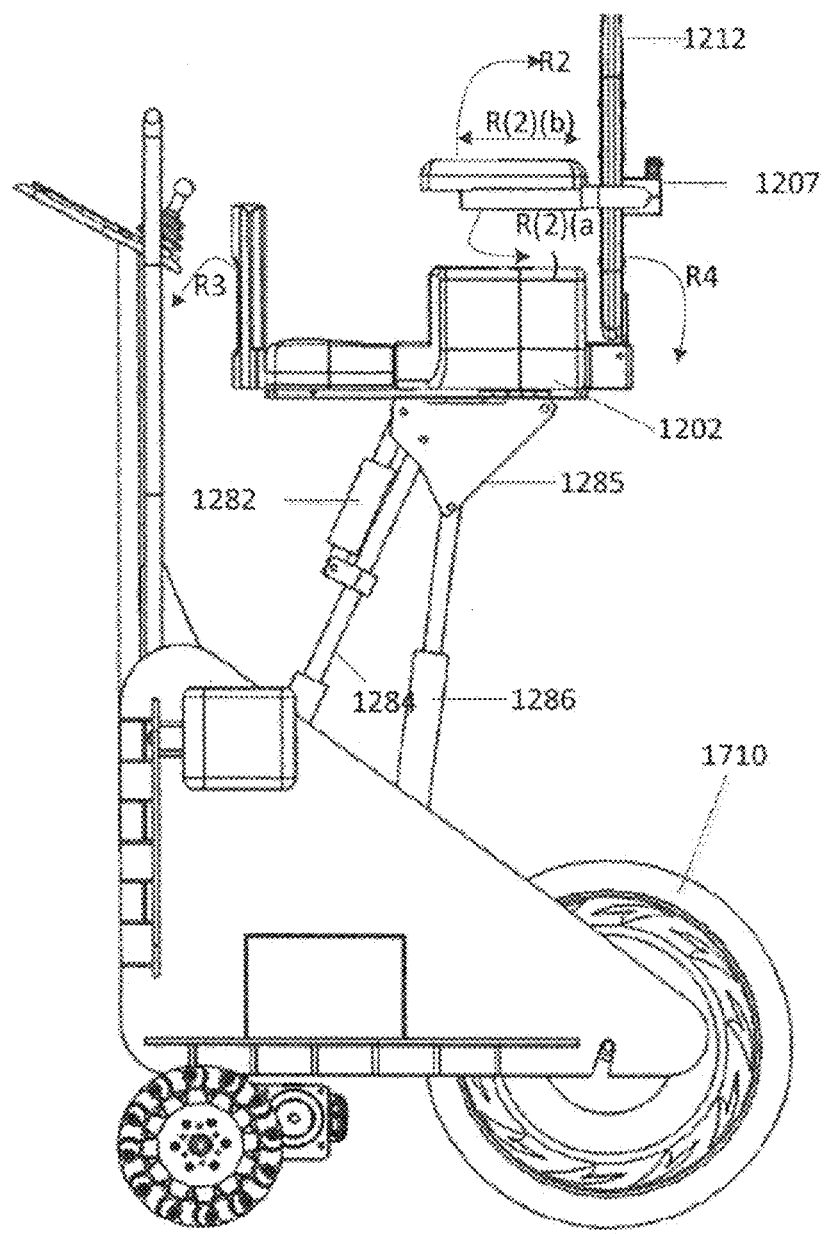
FIGS. 3A-3B illustrate side views of the mobility device of FIG. 1.
Figure 3B:
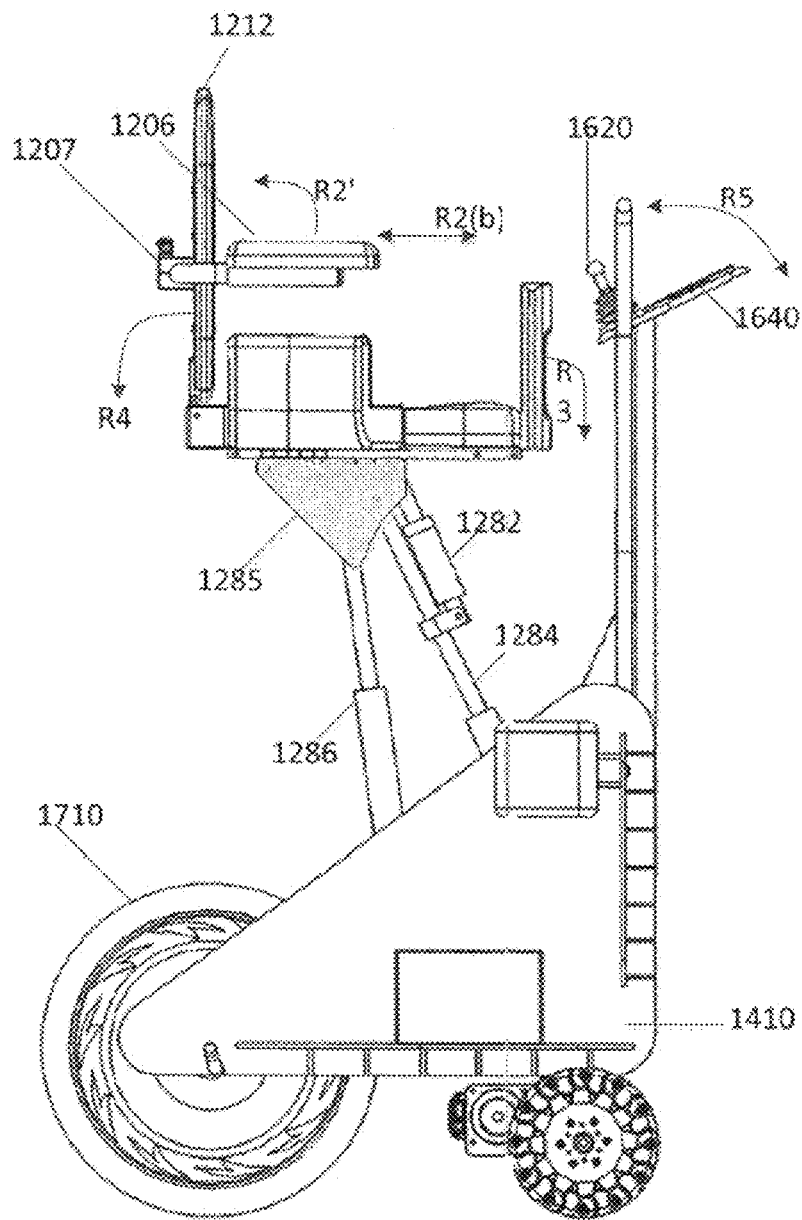

FIGS. 3A-3B illustrate side views of the mobility device of FIG. 1. As shown in FIGS. 1 and 2 the seat can, in one configuration, be positioned such that it is, for example, in an x-y plane. The back support 1212 is rotatably connected to the main seat body 1202. The back support 1212 rotates in the direction of R4 from a position that is perpendicular, or substantially perpendicular, to the main seat body 1202 to a position that is planar, or substantially planar, to the main seat body 1212. This function allows the user to access the device from and to a bed, a toilet, and any other flat surface from where the user needs to access the device. The back support 1212 has one or more apertures 1214, 1216, 1216', as mentioned above. In operation, for example aperture 1214 enables a user to grip the back support 1212 and pull the back support 1212 and/or pull the user towards the back support 1212. The user then may roll onto the seat of the device to be fully mounted on the device.

Additionally, one or more rollers 1218, 1218' can be provided within the back support 1212 to facilitate rolling along the length of the back support 1212 by a user as described below.

The side arms 1206, 1206' can be connected to an associated side arm bracket 1207 which engages the back support 1212. The one or more side arms 1206, 1206' are configurable such that the side arms 1206, 1206' can be in the same plane as the main seat body 1202 in a first configuration, and rotated upwards in the direction of R2, R2' into a position that is perpendicular to the main seat body 1202. Additionally, or in the alternative, the side arms 1206, 1206' can be rotated downwards in the direction of R2(*a*), R2(*a*)'. Additionally, the length of the side arms 1206, 1206' can be adjusted by sliding the arms in the direction of R2(*b*) backwards and forwards. Any of the side arms 1206, 1206' and the main seating body 1202 can be provided with padding to provide a soft surface to engage the user.

The frontal arch 1208 is connectable to the main seat body 1202 so that the frontal arch can rotate in the direction of R3 from a first position which is perpendicular, or substantially perpendicular, to the main seat body 1202, to a second position which is parallel, or substantially parallel, to the main seat body 1202. As seen in FIG. 1, the frontal arch 1208 is further configurable to have an arch aperture 1210 formed within the frontal arch 1208 to enable a user to grab the frontal arch 1208 and wrap his or her fingers around the frontal arch 1208 to grasp the frontal arch 1208. The frontal arch 1208 can be positioned, rotated, slid, or tucked away to allow for front loading, as well as provide the user with a frontal support for when the user is tilted forward.

As mentioned above, the mobility device has seat system 1200 that may be a morphing, body adapting seat system. The seat can thus adjust to the body, size, and weight of the user to provide support and comfort. In one embodiment, the seat has an integrated cushioning system. In another embodiment, the seat provides a platform onto which a removable cushion can be adapted. In yet another embodiment, the seat cushioning can be regulated automatically or by the user to provide better fitting and support to the user or to relieve pressure or avoid pressing specific parts of the user that are in contact with the seat.

The handle bars 1610, 1612 can be moved in the direction of R5 in a forward and backward motion to propel the device when operating in a manual mode, as shown in FIG. 3B, for example. Additionally, a handbrake (not shown) can be provided on the handles 1614, 1616 to facilitate stopping the mobility device when in motion. Additionally, the handle bars 1610, 1612 can be push-pulled to achieve movement to the right or left by the user. For example, when the user pulls on the right handle while pushing on the left handle movement to the right is achieved. Conversely, when the user pulls on the left handle while pushing on the right handle, movement to the left is achieved. In such embodiment, the handles 1614, 1616 and handle bars 1610, 1612 can be articulated, expandable, retractable, folding and/or pivoting to adapt to the user needs and to be moved away.

Additionally, the mobility device may have electronic controller 1620 or an alternative mechanism for controlling motion, as mentioned above. The user can use the electronic controller 1620 to electronically drive, steer, and control the device. In such embodiments the user can choose to drive the device in a completely human powered mode, in an electronically controlled mode or in a hybrid mode combining human power and electronic control.

Figure 4:
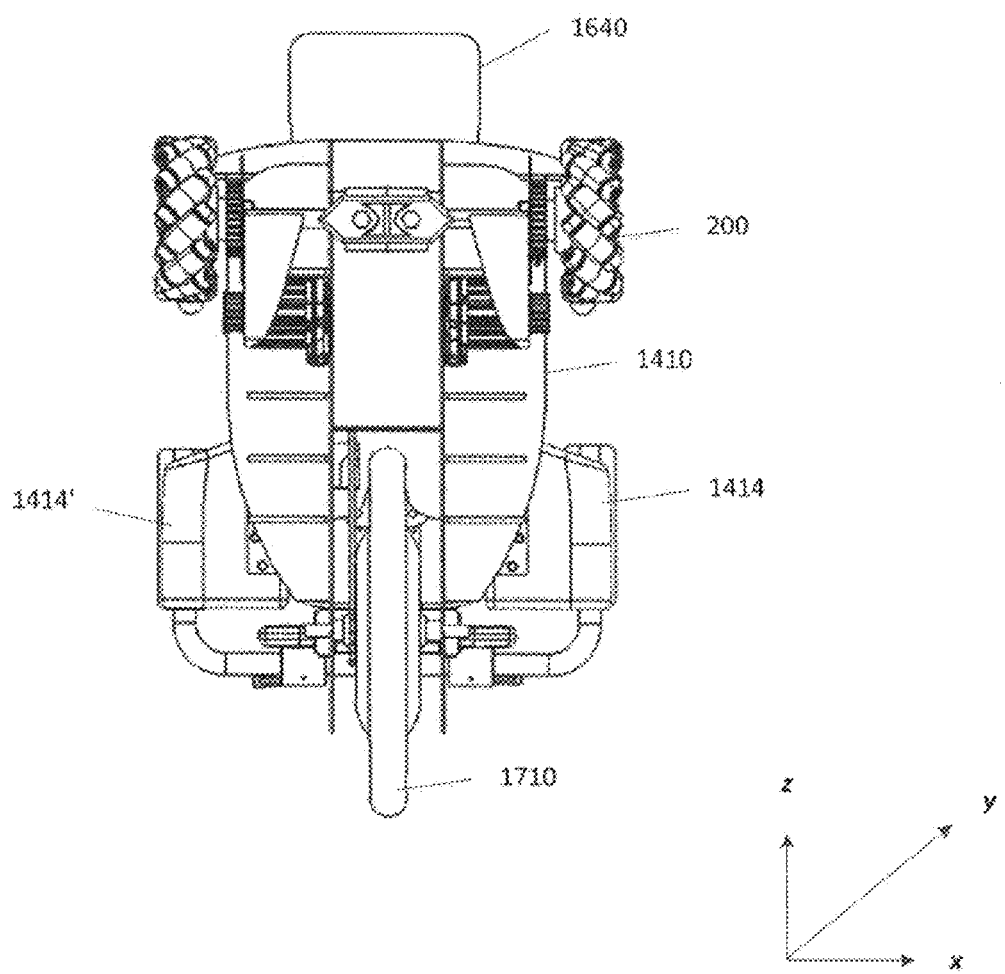
FIG. 4 illustrates a bottom view of the mobility device of FIG. 1.

FIG. 4 illustrates a bottom view of the mobility device of FIG. 1.

Figure 5:
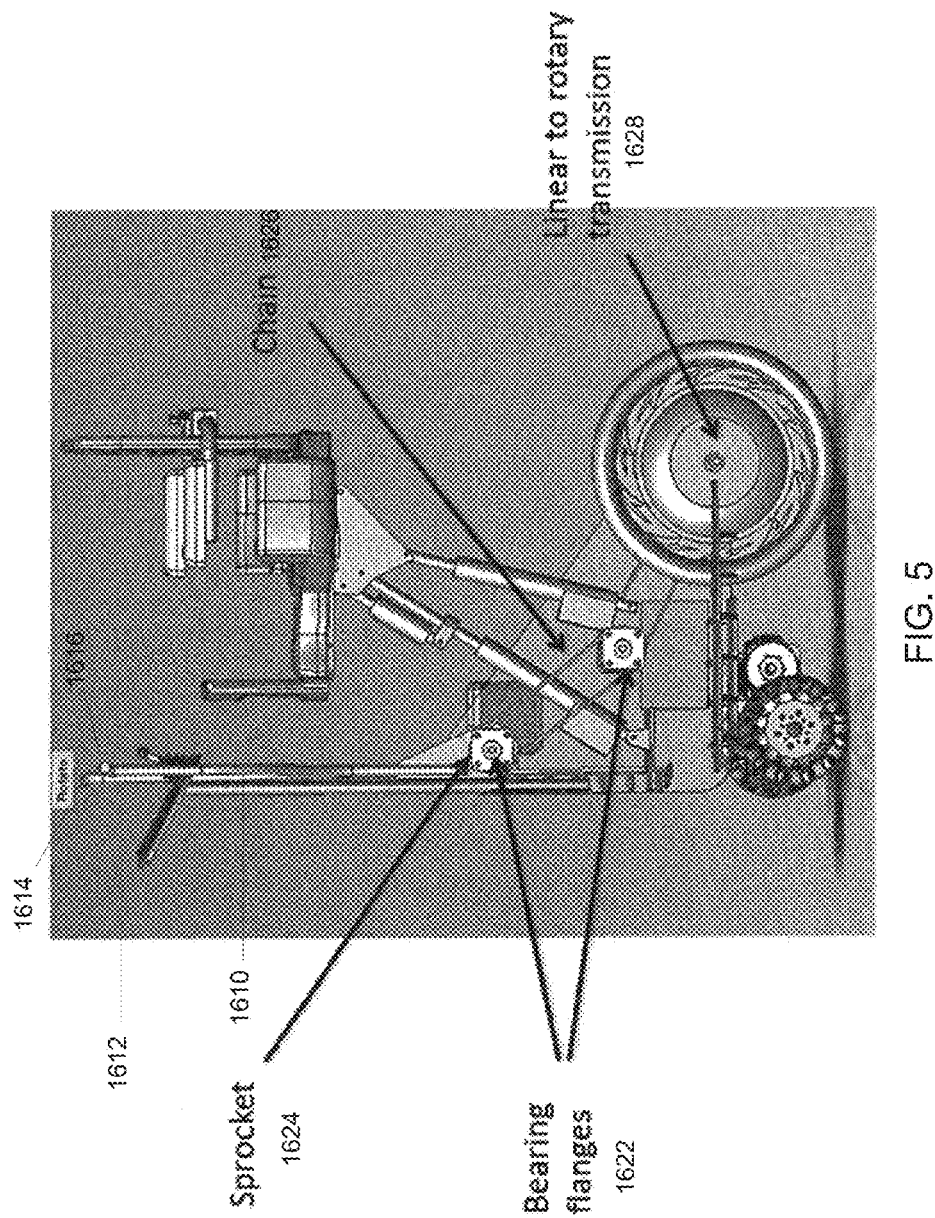
FIG. 5 is a perspective view of a control system of a mobility device according to some embodiments of the disclosed technology.

FIG. 5 illustrates the various components of an embodiment of the manual drive operation using handle bars 1610, 1612. For manual drive operation in this embodiment, handle bars 1610, 1612 connect via bearing flanges 1622 shown in FIG. 5 to a front-centered sub-frame element in which a sprocket 1624 holds a chain 1626 that connects to the main center wheel 1710, like in a bicycle, and allows for manual movement that propels the device with a push-pull motion of the handle bars 1610, 1612. The chain and wheel system has a linear to rotary transmission system 1628 that reduces the effort to move the wheel requiring less arm pull/push to move the wheel, thereby reducing the strain on the user's shoulders. Either handle 1614 or handle 1616 can be rotated and such rotation is translated through the cables into a rotation of the front wheels. However, the handle bars 1610, 1612 may connect to mobility device in any manner that provides a user to use the handle bars 1610, 1612 to manually operate the mobility device.

Figure 6C:
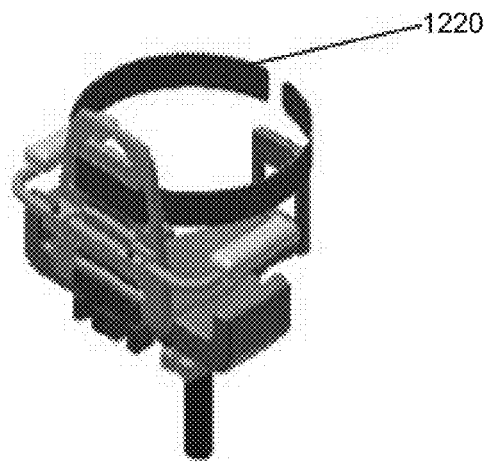
Figure 6D:
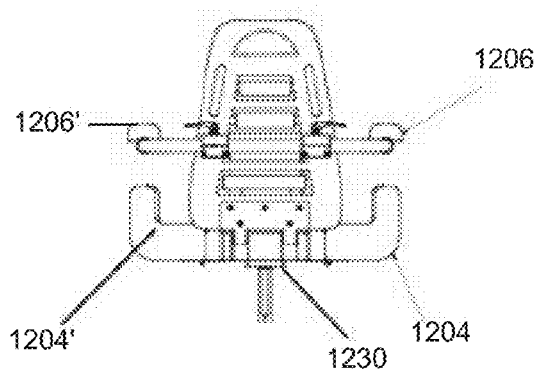

FIGS. 6A-6E illustrate some positions of the seat system 1200 according to some embodiments. In one aspect, the back support 1212 pivots in the direction of R4, as shown in FIGS. 3A-3B, so that it is in the same plane as the seat 1202, as seen in FIG. 6A. The seat wings 1204, 1204' are rotated downward in the direction of R1,R1', and the side arms 1206 are rotated up or down. The user then positions him/herself so that his/her legs approach the frontal arch 1208 and pulls him/herself towards the frontal arch 1208 by grasping the frontal arch 1208 around the aperture 1210 through the arch. Once the user's buttocks is on the seat 1202, the back support 1212 can be pivoted upward in the direction of R4, as seen in FIGS. 3A-3B and 6B, so that it is perpendicular to the main seat body 1202. The seat wings 1204, 1204' can be rotated to provide a perpendicular surface to the user's legs when seated. The side arms 1206, 1206' are then rotated to be positioned parallel the seat at a location where the user's arms would naturally fall when the arm is bent at the elbow. As seen in FIG. 6C, the back support 1212 may also contain slits 1216, 1216', as discussed above, to attach strap 1220 to stabilize the body of the user.

In some embodiments, the seat system 1200 is connected to the control system 1600 through a seat base 1230. The seat base 1230 provides a platform for the seat and cushion. Such seat base is may be connected to the control system 1600 using a seat joint system 1280 that allows the seat to tilt and rotate in any direction, which will be discussed in more detail below.

Figure 6E:
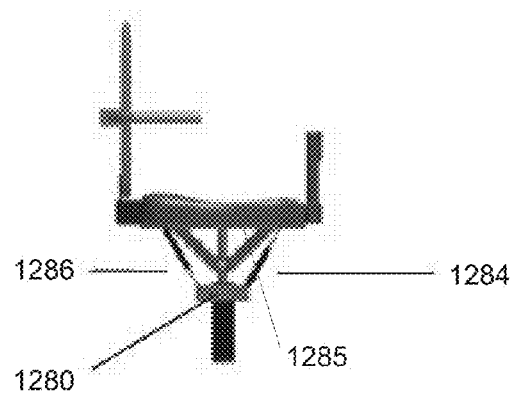
Figure 7E:
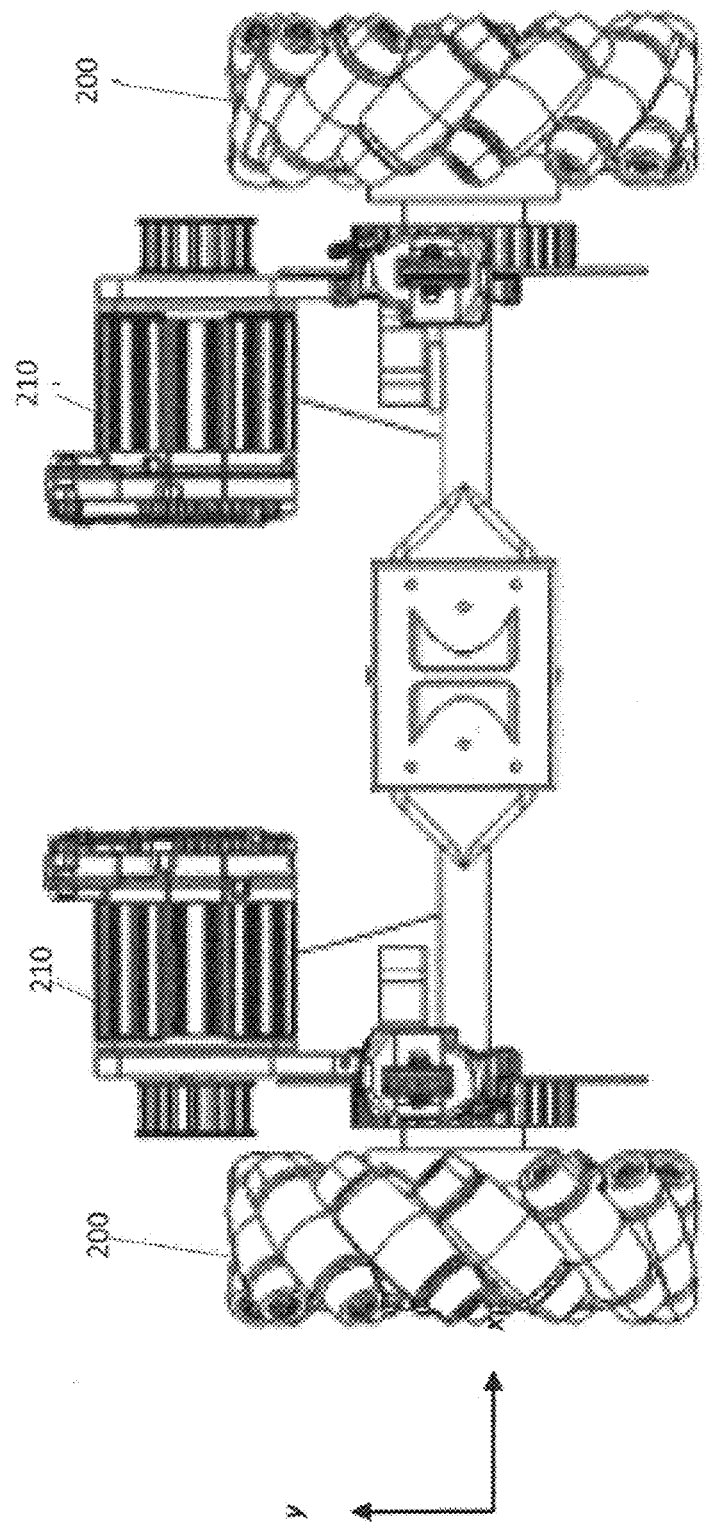

In some embodiments the main seat body 1200 is supported away from the base system 1400 by the control system 1600 through a set of actuators 1284, 1286, as seen in FIGS. 3A-3B and 6E. The actuators 1284, 1286 provide control over the seat position relative to the body of the device, allowing the device to convert from a seated device to a standing device. A tilt actuator in the seat joint system 1280 is connected to a front linear actuator 1284 which is adjacent a rear linear actuator 1286, which will be discussed in more detail below. The front linear actuator 1284, and the rear linear actuator 1286 may further engage an articulating seat bracket 1285 which is affixed to the lower surface of the main seat body 1202.

While on the mobility device the user can choose the positioning, lower level (sitting) or upper level (elevated). To alternate between positions the user has different ways to modulate the height (joystick 1620, console 1640, manual 1610, 1612). In the sitting position the rear linear actuator 1286 will be compressed to its shortest length. When elevating, the rear linear actuator 1286 will extend up to the maximum length, the frontal linear actuator 1284 will in turn shorten. The tilt linear actuator 1282 will allow the user to bend slightly forward (mainly useful when in elevated position) or to recline backwards (mainly useful when in a seated position).

Other embodiments of foldable seats with different folding configurations and designs can also be used. The folding capabilities of the seat may reduce the spanning seat surface facilitating the user an easy mount from or to the front of the mobility device and from and to the back of the mobility device. Once the user has mounted or dismounted the device, the seat will be extended to regain its full size and provide full support to the user, if needed.

In another embodiment, the back support 1212 is connected to the base system 1600 or, alternatively, to a robotic elevation system 2800, discussed in detail below, through a bar that controls the position of the backrest. In such embodiment, the backrest can be lowered from a 90 degree position to 180 degree position (parallel to the ground) or up to a 270 degree position, perpendicular to the ground, remaining under the seat. In such position allowing the user to mount or dismount through the back of the seat.

Turning back to FIG. 1, the base system 1400 has a main sub-frame 1410 which has a pair of platforms 1412, 1412' upon which a user can place his or her feet. A pair of knee supports 1414, 1414' is provided into which a user's knees can be placed. The knee supports 1414, 1414' adjust depending on whether the device is in a seated configuration or a standing configuration. Structural supports 1420 are provided to provide integrity to the structure and a solid anchor for the knee support. Additionally, an exterior body (not shown) can be positioned around the base 1400 which closes the device and can also provide a customizable/decorative aspect to the device.

Three wheels 1710, 200, 200' are provided in the base system 1400. A first wheel 1710 is positioned centrally under the seat system 1200. A pair of front/control wheels 200, 200' are positioned forward the front wheel 1710. The pair of front/control wheels 200, 200' provide steering and control, as discussed below.

The pair of front/control wheels 200, 200' can be Mecanum wheels. A Mecanum wheel is a conventional wheel with a series of rollers attached to its circumference. The rollers typically have an axis of rotation of 45 degrees to the plane of the wheel and at 45 degrees to a line through a center of the roller parallel to an axis of rotation of the wheel. An advantage of the Mecanum wheel is that the device will have increased flexibility in terms of direction of movement. For example, running the wheels on one side in the opposite direction of the wheels on the other side, causes rotation of the device. Running the wheels on one diagonal in a direction that opposes the wheels on the other diagonal will cause sideways movement. As will be appreciated by those skilled in the art, combinations of wheel motions allow for vehicle motion in any direction with any wheel rotation.

FIGS. 7A-7F illustrate of a portion of a configuration of a mobility mechanism for the mobility device. In this configuration, each of the front Mecanum wheels 200,200' are connected through a hub 206, 206' (that holds the wheels 200, 200' to the corresponding bearing 204, 204' and corresponding disc brake 208, 208') to a corresponding brushless DC electric motor 210, 210'. A front wheel pivoting axle 230 connects the two Mecanum wheels. Suspension spring elements 240, 242 are provided between the axle 230 and a subframe 1410, and housed by a truck 250 to provide mechanical buffering between the user and any rough terrain that the device may be travelling on.

Figure 8A:
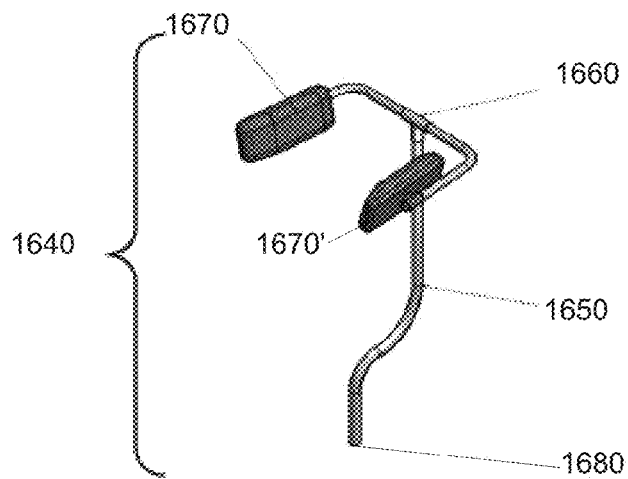
FIGS. 8A-8B are perspective views of an alternative control system of a mobility device according to some embodiments of the disclosed technology.
Figure 8B:
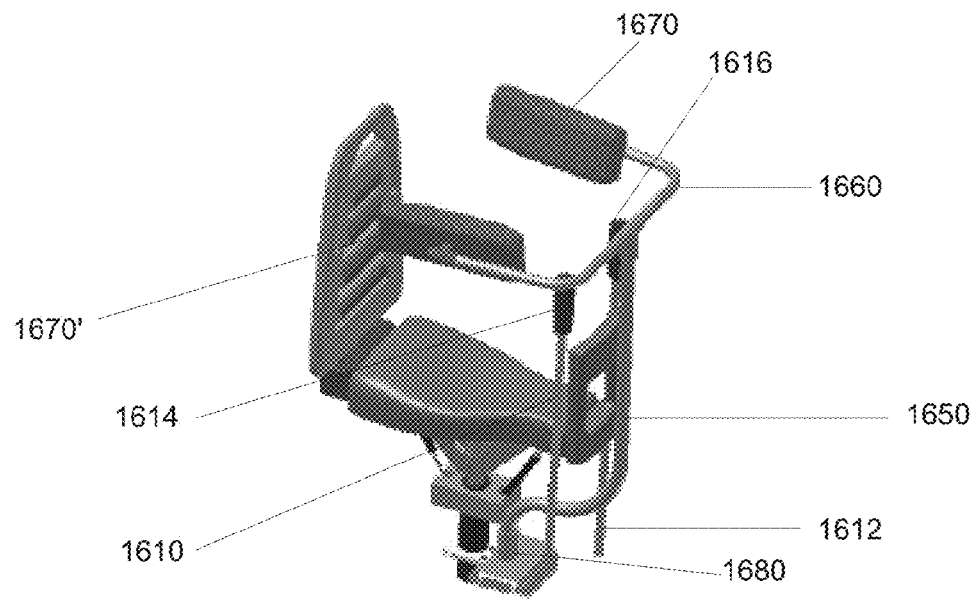

FIGS. 8A-8B shows perspective views of an alternative embodiment of the mobility device with a body-controller system steering system 1640. This steering system contains a vertical bar 1650, connected to a horizontal bar 1660 with two underarm pads 1670, 1670'. FIG. 8B shows a side view of one configuration of the body-controlled system.

Side arms 1670, 1670' which enable a user to steer and control the movement of the device 10 by moving his or her torso with the side arms 1670, 1670' engaged under the user's arms. For example, the each of the side arms may include a pressure sensor (not shown). When a user puts pressure on one of the side arms 1670, 1670', the processor connected to the control system 1600 is able to translate this pressure and determine which direction to move and how fast to move the mobility device. In other embodiments, a strain gauge may be provided at a front and side surface at a bottom portion 1680 of the vertical bar 1650 that connects to the base system 1400. The user may press on the vertical bar 1650 or the side arms 1670, 1670' to indicate which direction to move the device. Further, the amount of pressure applied indicates the speed to move the device. The greater the pressure, the greater the speed the mobility device moves. This steering mechanism can be used as well to hold the user's body when he/she wants to be above the seat level without elevating the seat by using the force of the underarms. The body steering mechanism 1640 can be rotated downwards to be tucked away under the seat system 1200. As with the other configurations, foldable/retractable arm rests 1206, 1206', are provided, along with a foldable/retractable back support 1212.

Figure 9:
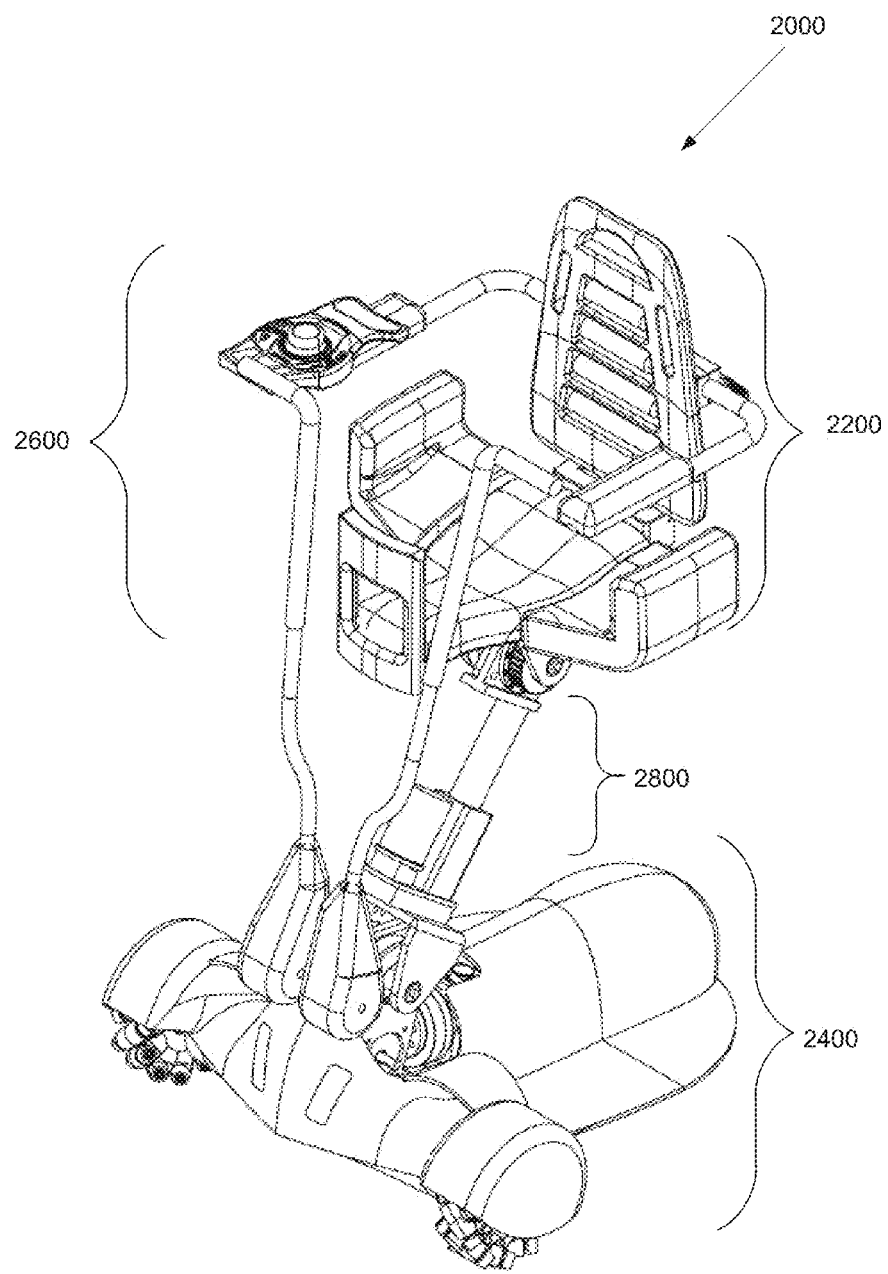
FIG. 9 is a perspective view of another embodiment of a mobility device according to the disclosed technology.

FIG. 9 illustrates an alternative embodiment of a mobility device 2000. As a non-limiting example mobility device 2000 can include a seat system 2200, a base system 2400, a control system 2600, and a robotic elevation (arm) system 2800. Similar to mobility device 1000, mobility device 2000 is configured to provide transitioning from sitting to standing, drive the device manually or electronically, in any direction, and assist in rehabilitation. In one embodiment, while on the mobility device the user can choose the positioning, lower level (sitting) or upper level (elevated). To alternate between positions, the user has different ways to modulate the height, as discussed above. The user has a broad range of functionalities with the device including using the device for transportation in a sitting position as well as in a standing supported position, and in any intermediate position. The user can drive the device using human propulsion through handles or can drive the device electronically, either via a joystick or via a computer interface. Additionally the user can drive the mobility device forwards, backwards, or sideways or turn or rotate any direction the user needs. Furthermore the user can choose and control the speed of movement. Moreover, the user can use the intelligent capabilities of the device for multiple actions, including but not limited to, the motion and operation of the device, as well as the connectivity functions the computer interface provides, such as connectivity to other users, people, technical support, etc. The user can use manual, voice, hand, eye, body motion commands and additional assistive technology to operate the different functionalities included in the device.

Any of the seat system 2200, the base system 2400, and the control system 2600 can be any of the base system 1400, the seat system 1200, and the control system 1600 discussed above with respect to mobility device 1000.

Figure 10:
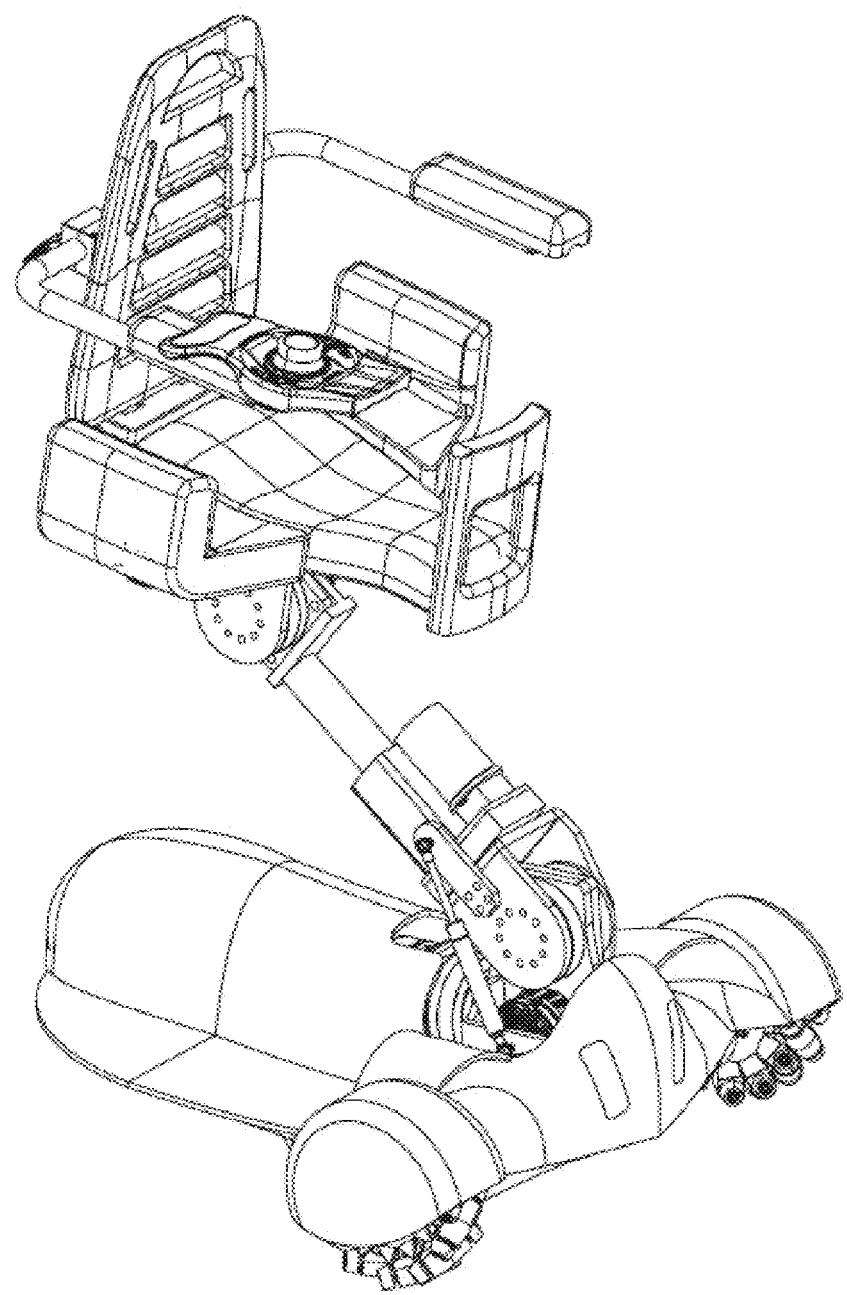
FIG. 10 is a perspective view of another embodiment of a mobility device according to the disclosed technology.

As mentioned above, FIG. 9 illustrates a mobility device 200 including both a manual and an electronic control system 2600. FIG. 10. Illustrates an alternative embodiment of the control system 2600 of the mobility device 2000. In these embodiments, only an electronic control system 2600 is provided and the manual drive system discussed above is removed.

The control system 2600 includes a controller (not shown) electrically connected to the base system 2400 and the robotic elevation system 2800. The controller receives signals from the control system 2600 based on the user input for a desired direction of motion, and the controller sends control signals to the various components of the base system 2400 and the robotic elevation arm system 2800 to effectuate the movement.

Figure 11B:
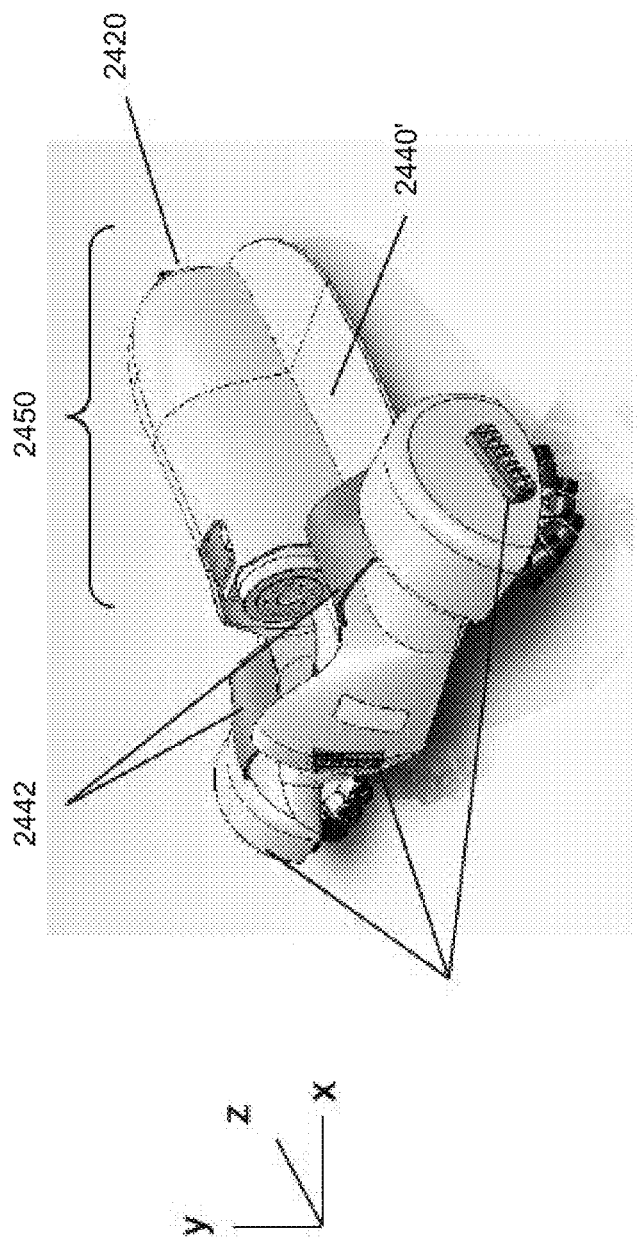

FIGS. 11A-11B illustrates one embodiment of base system 2400. Referring to FIG. 11B, in one embodiment the base system 2400 has a main subframe, which has a pair of platforms 2440, 2400' upon which a user can place his or her feet. A pair of knee supports (not shown) may be provided into which a user's knees can be placed. The knee supports adjust depending on whether the device is in a seated configuration or a standing configuration. Additional structural supports may be provided to provide integrity to the structure and a solid anchor for the knee support. Additionally, an exterior body 2450 can be positioned around the base system 2400 which closes the device and can also provide a customizable/decorative aspect to the device.

Base system 2400 also includes an omnidirectional drive system. Although the omnidirectional drive system is shown with the mobility device 2000, omnidirectional drive system may be used with any other device or system that requires movement. In one embodiment omnidirectional drive system can includes two Mecanum wheels 2410, 2410', a central rear omnidirectional wheel 2420, as well as axis1 2810 of the robotic elevation system 2800, discussed below. This omnidirectional drive system allows the movement of the mobility device in any direction or rotation of the X and Z plane, as discussed in more detail below. The wheels can be substituted for other non-omnidirectional wheels or wheels for all terrain access or for water access. This will allow the user to access a multitude of terrain types.

The base system 2400 has two foot rests 2440, 2440', one on each side that adjust to the feet size and position of the user. The foot rests may contain straps 2442 that can be adjusted to the user needs. In addition, connected to the base, the mobility device 2000 may include the knee supports discussed above. The knee support can have one or more sets of straps that adjust to the legs of the user. Both footrests and knee supports can be adjusted, customized, exchanged, or removed to fit the user needs.

The base system 2400 houses the unit's battery (not shown) and motors 2490. Multiple batteries may be used rather than a single battery. The base system 2400 and robotic elevation system 2800 may have exterior bodies (shells) 2450 covering the internal mechanisms. In one embodiment, the base system 2400 can be configured, designed, and built in modules that can be mounted, changed, replaced, or adjusted independently.

Turning back to the omnidirectional drive system, each of the front Mecanum wheels 2410, 2410' are connected through a hub (that holds the wheels to the bearing and disc break) to the corresponding brushless DC electric motor 2412. The Mecanum wheels 2410, 2410' include the same components as shown in FIGS. 7A-7E and therefore are not discussed in more detail here. The Mecanum wheels 2410, 2410' and the rear omnidirectional wheel 2420 are connected to the corresponding brushless DC electric motor 2412 through a damping element to provide vibration isolation to the mobility device and allow a smoother ride for the user.

In this configuration, the user can move or drive laterally, in which case the Mecanum wheels 2410, 2410' and the rear omnidirectional wheel 2420 will rotate in such a way that the device will drive in a completely lateral direction. Additionally, the user could rotate around a central position, in that case, the Mecanum wheels 2410, 2410' will move laterally in one direction while the rear omnidirectional wheel 2420 does not move. The Mecanum wheels 2410, 2410' may be provided on a single axel or may be provided on separate axels that are located on the same axis.

The central rear omnidirectional wheel 2420 may be a single omnidirectional wheel or may be composed of a plurality of stacked omnidirectional wheels, as shown in FIG. 11A. The two Mecanum wheels 2410, 2410' are located rotate about a first axis and may be mounted on a single axel or on two separate axels. The central rear omnidirectional wheel 2420 rotates about a second axis that is perpendicular to the first axis.

Each wheel 2410, 2410', and 2420 moves and is controlled independently of the other wheel. Mecanum wheels 2410, 2410' are located on an axis that is perpendicular to the axis of the rear omnidirectional wheel 2420. This allows the controller to determine any pivoting point upon which to move. Controlling each of the wheels 2410, 2410', and 2420 allows the user to move in any desired direction, including a completely lateral movement or a rotational movement. That is, the mobility device may rotate, swerve, or weave side-to-side while moving in a forward, backward, lateral, or diagonal motion. This allows a user to move the device in a fluid motion in any desired direction. This allows the mobility device to mimic the flowing movement of dance, for example.

FIGS. 12A-12D shows views of a robotic elevation system 2800 of the mobility device according to some embodiments. The robotic elevation system 2800 may be used in place of actuators 1284, 1286 discussed above. Robotic elevation system 2800 is connected to the seat system 2200 and holds the main seat body. The robotic elevation system 2800 lowers the seat close to the base system 2600 and elevates the seat system 2200 to a raised position allowing the user to move from a low seated position to a supported standing position following an ergonomic movement.

The robotic elevation system 2800 connects to the base system 2600 through a joint system. Although the robotic elevation system 2800 is shown with the mobility device 2000, the robotic elevation system 2800 may be used with any other device or system that requires a robotic elevation system. The joint system includes four axes: axis1 2810, axis2 2820, axis3 2830, and axis4 2840. The base system 2400 provides a means of angular rotation around the X and Z axis of the robotic elevation system 2800 to allow translational movement of the robotic elevation system 2800 in a given plane, usually orientated vertically. The robotic elevation system 2800 bends along its joints 2850 to allow an end effector 2860 of the robotic arm to translate in a line at a predetermined angle Θ with its vertical translation, as shown in FIGS. 12B and 12D. That is, axis 1 2810 pivots about an axis that is parallel to the axis the rear center wheel 2420. This allows the end effector 3860 to move in a left and right direction, as shown in FIG. 12D. Axis3 2830 of robotic elevation system 2800 is capable of extending and retracting via a linear actuator to achieve a greater range of motion coverage. The linear actuator of axis3 2830 may be, for example, a pneumatic cylinder or a hydraulic cylinder. However, the disclosed technology is not limited by such, and the linear actuator of axis3 2830 may be any type of known linear actuator The robotic elevations system 2800 can perform its horizontal and vertical translations separately or simultaneously. At the end of the robotic arm 2840 is the end effector 2860 to allow for the adaptation of a multitude of seats or accessories.

Further, a nitrogen filled gas spring may be provided to assist the robotic elevation system in providing torque to counter balance the weight of a user as the robotic elevation system is adjusting.

In one embodiment, the end effector 2860 contains sensors that monitor the cushion pressure, as well as monitor other metrics, such as the time that the user has been in seated position, the time since the user last moved, the temperature of the user, the weight of the user, the distance of the user to the ground, etc. For example, the end effector 2860 may contain four load sensors (not shown). The load sensors are able to determine the weight of a user using a summation across all four load sensors and able to provide additional information, such as if a user has shifted to the left or right based on the signals from the load sensors. The seat system 2200 may be attached the end effector 2860 such that the seat system 2200 may be independently rotated from the end effector 2860 to allow the user to rotate the seat, rather than the mobility device as a whole.

Axis1 2810, axis2 2820, and axis4 2840 may include angle measuring sensors to track the position of the axes. Axis3 2830 includes a linear measuring sensor to track the distance of the extension, as well as the rotation of the axis. The angle measuring sensor may be, for example, a potentiometer or a rotary encoder while the linear measuring sensor may also be a potentiometer or a glass slide. The angle measuring sensors and the linear measuring sensors of each of the axes is able to determine the position of its respective axis and send the determined position to the controller. In some embodiments, the angle measuring sensors and the linear measuring sensor perform an absolute measurement so that the sensors need not be zeroed if the device turns off and then back on to determine their position. Based on this information, the controller is able to determine the position of the end effector 2860 to determine the position of the seat system 2200. The robotic elevation system 2800 allows the controller to move the various axes of the robotic elevation system 2800 in a movement that is ergonomic and natural for a user. That is, if a user desires to stand or sit, the robotic elevation system 2800 is able to move each of the individual axes to allow the user to stand or sit in the same manner as an individual that is not using a mobility device.

The controller receives the various signals from the angle measuring sensor, linear measuring sensor and other sensors, such as a weight signal, and is able to determine a correction amount to make to the robotic elevation system prior to a desired movement of the user to keep the center of gravity of the mobility device above the base system 2400 at all times. This helps prevent the user from accidentally tipping the mobility device and helps keep the user at a desired position when moving the mobility device. Preferably, the controller receives input of data regarding its position relative to the earth, the position of the robotic elevation system 2800, and feedback from the sensors on the end effector 2860 to keep the center of gravity of the mobility device over the base system 2600 or the ground at all times.

Further, in some embodiments, the controller determines minute movements for each of the axes of the mobility device throughout the day to provide therapeutic benefits to a user, while maintaining the center of gravity. That is, when the mobility device is not moving in a controlled direction by a user, the mobility device may make minute adjustments throughout a day to relieve muscle soreness or pressure. These individual adjustments are not felt by a user as they are made.

Inside, outside, or integrated in the base system 2400, as well as in the robotic elevation system 2800 or any part of the mobility device there may be a series of sensors installed. The number of sensors may vary from one to as many as needed, and will depend on the specific needs for the function of the device. Each of the sensors will connect to either the central module or the peripheral modules, engines or motors, controls of the device, discussed in more detail below, and will communicate with the controller of the mobility device connected to the computer interface 2640. Such sets of sensors can be a minimum of one set for the front wheels 2810, 8210, one set for the rear wheel 2420, one set for lights, one set for obstacle detection, etc., up to many sets including sensors to detect environmental cues, such as temperature, humidity, pressure (atmospheric or physical), etc. The signals from the sensors are sent to the controller to control the various electronic systems, including the base system 2400, the control system 2600, and the robotic elevation system 2800.

The robotic elevation system 2800 comprised of the three rotation axes axis1 2810, axis2 2820, and axis4 2840 and the linear axis axis3 2830 are in such a configuration that axis1 2810 connecting the lower end of the robotic arm to the base system 2400 allows for lateral mobility (X axis from a front perspective of the mobility device) of the robotic elevation system 2800, axis2 2820 allows the robotic elevation system 2800 to elevate from a lowered position (0°) to a fully raised position (90°) (on the Z axis) while moving forward (or backwards) along the Y axis. Axis3 comprising the linear actuator allows an extension of the length of the robotic elevation system from a retracted position to an extended position and axis4 2840, connecting axis3 2830 with end effector 2860, allows a rotation of the end plate (forward and backwards). Each of these movements are determined by an input at the control system 2600, which can be a manual input or an electronic input, as discussed above.

The end effector 2860 may connect to a seat system 1200 or 2200 of a mobility device. Axis1 2810 allows a user to tilt the seat left or right along an X axis, if looking at the device from the front perspective. Axis2 2820 allows a user seated on the seat system to move forward from a back seated position to a forward seated position. Axis3 2830 allows the user to transistion from a seated position to an upright position, and vice versa while axis4 2840 allows the teach to tilt forward and backwards. This provides the user with a natural and ergonomic transistion from a lower seated position to an upright standing position, or vice versa, and any lateral tilt or combined orbital movement.

Figure 13A:
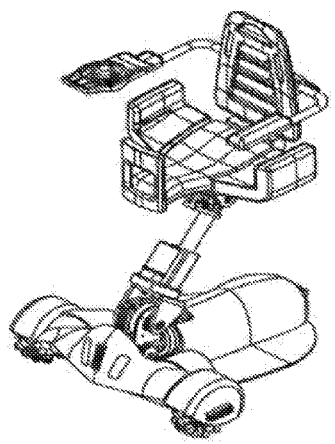
FIGS. 13A-13F are perspective views of various configurations of a mobility device according to some embodiments of the disclosed technology.
Figure 13B:
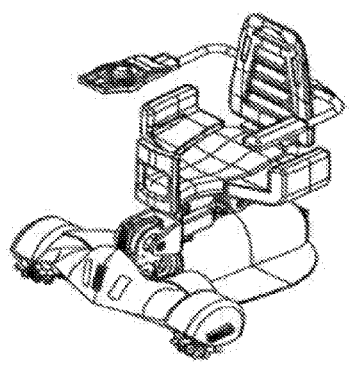
Figure 13C:
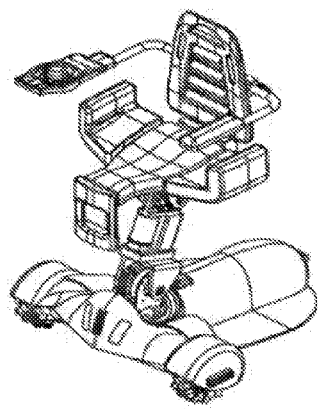
Figure 13D:
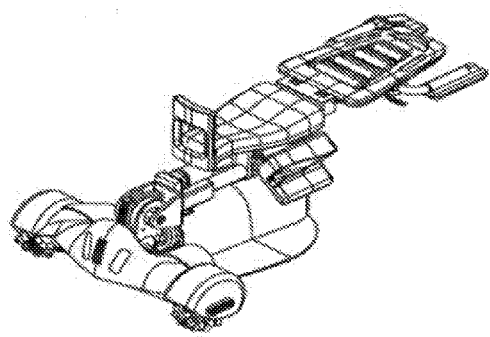
Figure 13E:
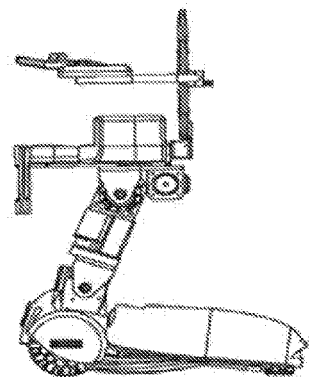
Figure 13F:
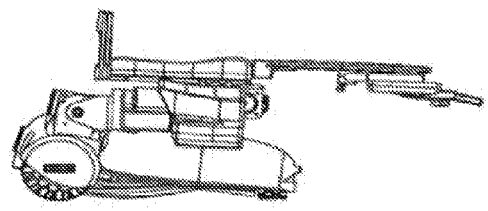

FIGS. 13A-13D are elevation views of the mobility device 2000 showing different modes of the seat system 2200 and the robotic elevation system 2800. FIGS. 13A and 13E illustrate the mobility device in an elevated/standing position. FIG. 13B illustrates the mobility device in a fully seated position. FIG. 13C illustrates the mobility device in a slightly elevated position. FIGS. 13D and 13F illustrate the mobility device in a full seated position with the back rest 1210 substantially parallel with the main seat body 1202 to allow a user to enter the mobility device.

Figure 14:
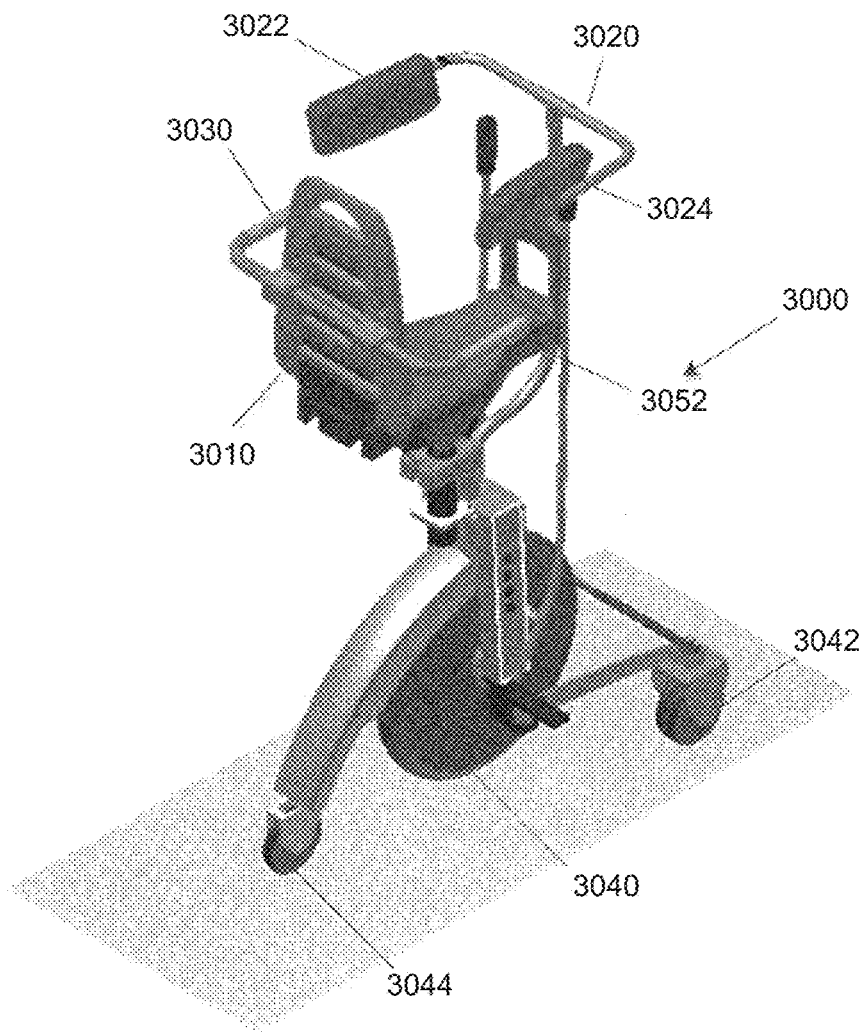
FIG. 14 is a perspective view of an alternative embodiment of a mobility device of the disclosed technology.

FIG. 14 is a perspective view of an alternate embodiment of a mobility device 3000. In this configuration, a steering mechanism 3020 is provided which includes side arms 3022, 3024 which enable a user to control movement of the device 3000 by moving his or her torso with the side arms 3022, 3024 engaged under the user's arms, similar to FIGS. 8A-8B discussed above. This steering mechanism can be used as well to hold the users body when he/she wants to be above the seat level without elevating the seat by using the force of the underarms. As with the other embodiments discussed above, foldable/retractable armrests 3030, 3032, are provided, along with a foldable/retractable back support 3012. The wheels include a center wheel 3040, a pair of front omni wheels 3042, and a rearward supporting back wheel 3044.

Preferably, in all of the embodiments discussed above, the mobility device has a compact design. The device width ranges between 12-25 inches in width, 22-35 in in length and 20-25 inches tall when in a sitting configuration and 30-40 inches when in a standing position measured from the ground to the base of the seat.

The systems and methods according to aspects of the disclosed subject matter may utilize a variety of computer and computing systems, communications devices, networks and/or digital/logic devices for operation. Each may, in turn, be configurable to utilize a suitable computing device, which can be manufactured with, loaded with and/or fetch from storage device, and then execute, instructions that cause the computing device to perform a method according to aspects of the disclosed subject matter.

A computing device can include without limitation a mobile user device such as a mobile phone, a smart phone and a cellular phone, a personal digital assistant ("PDA"), such as a BlackBerry®, iPhone®, a tablet, a laptop and the like. In at least some configurations, a user can execute a browser application over a network, such as the Internet, to view and interact with digital content, such as screen displays. A display includes, for example, an interface that allows a visual presentation of data from a computing device. Access could be over or partially over other forms of computing and/or communications networks. A user may access a web-browser, e.g., to provide access to applications and data and other content located on a web-site or a web-page of a web-site. A user may also communicate through the computing device with doctors, caretakers, family, friends, customer support and any other person, using systems such as Skype®, FaceTime®, and the like, using a video or a telephonic communication as well as via text, instant messaging and the like. The computing device may also send technical information to the customer support, related to the performance of the device, such as pressure, temperature, battery life, and any other information from the different components of the device, to provide the customer support information about the status of the device components.

Figure 15:
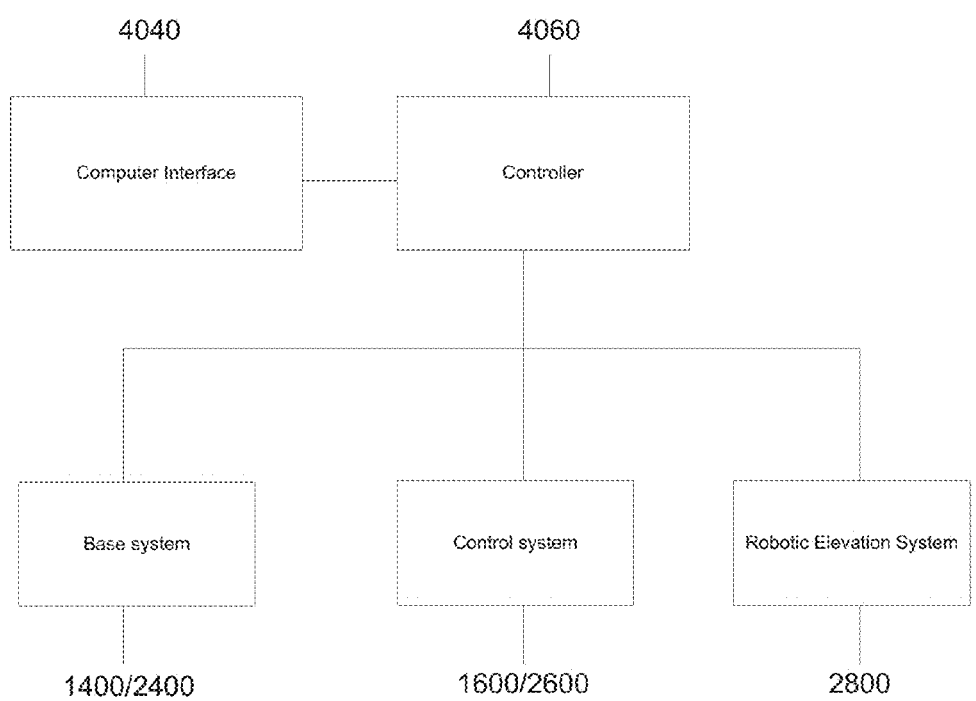
FIG. 15 is a flowchart illustrating an intelligence system according to some embodiments of the disclosed technology.

FIG. 15 is a representation for illustrative purposes of the intelligence system 400 components of any of the above-discussed mobility devices. The intelligence system 4000 includes a controller 4060, a computer interface 4040, the base system 1400/2400, the control system 1600/2600, and the robotic elevation system 2800.

Computer interface 4040 can be integrated into controller 4060, a mounted device, or it may be a separate entity. Computer interface 4040 determines the interface (communication) used to communicate to the processor 4050, or processing system 4060, discussed below. The driver software provides logic to the processor 4050, or processing system 4060, to further process data passed from the computer interface 4040. In such embodiment, the touch pad module 4240 incorporates the touch sensor, controller, driver software and the communication protocol as part of its interface with the intelligence system 4000. The display module 4260 then incorporates in addition to the standard display components, the touch sensor, controller, driver software and the communication protocol for the touch-sensitive overlay included into the display.

Figure 16A:
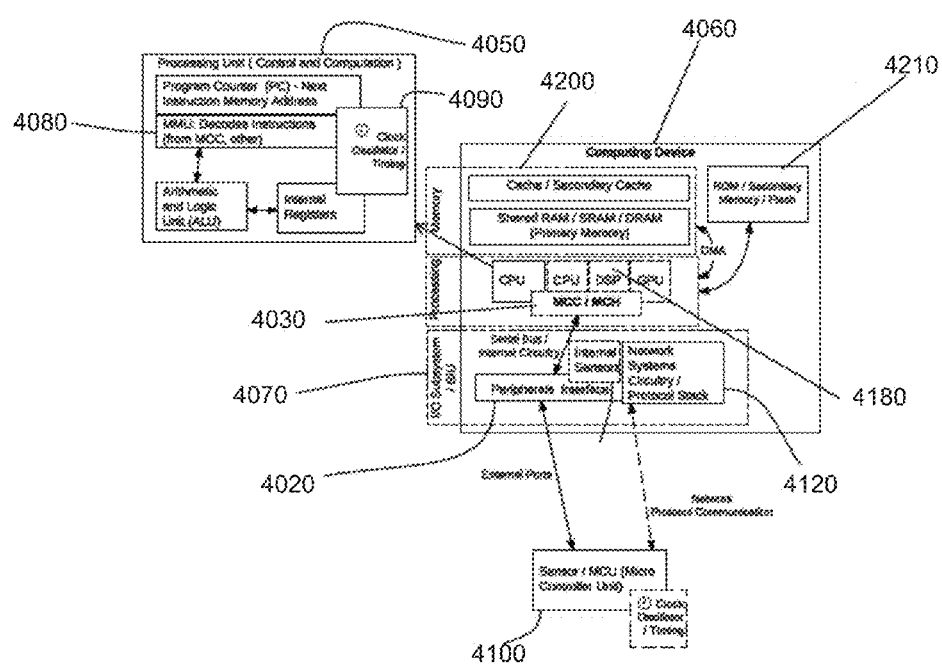
FIG. 16A-16C illustrate an intelligence system and user interface of a mobility device according to some embodiments of the disclosed technology.
Figure 16B:
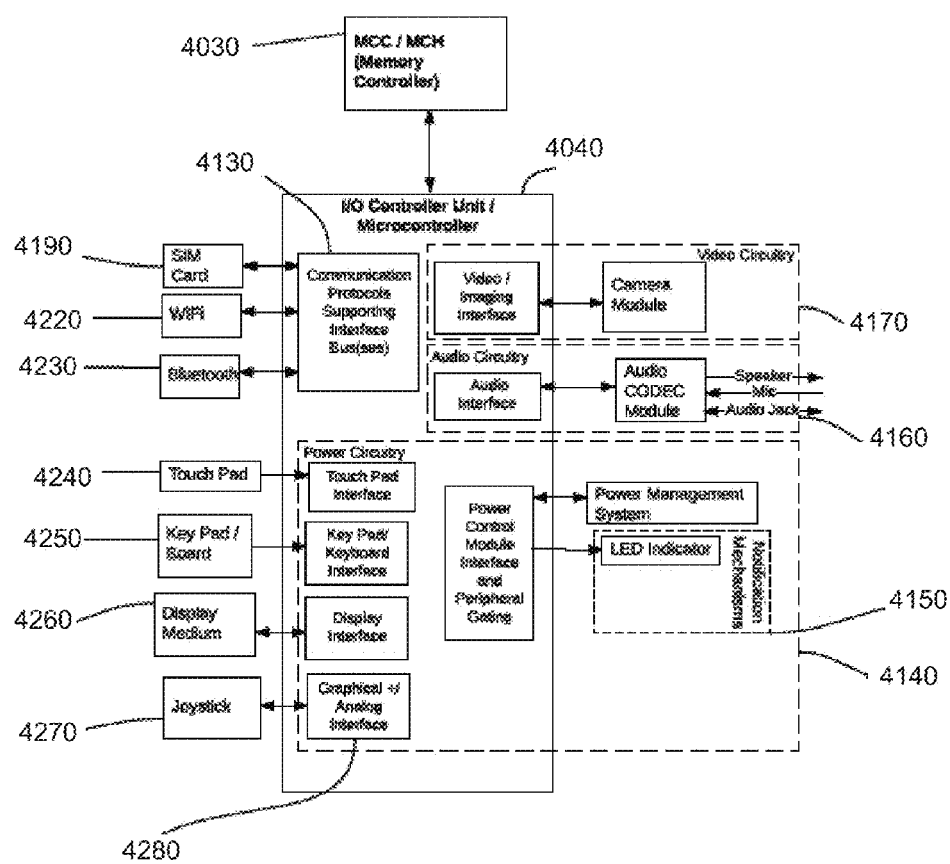

FIGS. 16A-16B are representations of one embodiment of the controller 4060, computer interface 4040, and their components. The controller 4060 includes computing device processor unit (CPU) 4050 or multiple processors as a processing system 4060 (CPU, GPU, DSP, etc bundled together) as in a SoC (System-on-Chip), possibly connected by a PCI (Peripheral Component Interconnect), as in a HSA (Heterogeneous System Architecture); the peripherals interface 4020, which might be utilizing a PCI bus or it might be a part of a PCH (Platform Controller Hub) and which includes the necessary technology to couple any of the input/output components or peripheral devices to a processing unit, including the utilization of the Bus Interface Unit (BIU) which is an integral part of the I/O subsystem 4070, an I/O Controller Unit 4040 or a Interface Controller Hub (ICH) responsible for controlling data requests and data flow to and from the I/O devices; a memory controller 4030, such as a memory chip controller (MCC), which can be integrated with the processor unit, as with Integrated Memory Chip (IMC), or it can be on a separate chip; some implementation of a memory management unit (MMU) which is usually incorporated per processor unit, especially as with a heterogeneous system architecture; timing, such as the RTC (Real-Time Clock(s) and/or a crystal oscillator), and which generally are responsible for setting and keeping a system clock 4090 which times any of the processes within a synchronous computing system; sensors 4100, 4110, can be external and/or internal to the computing device; the Network Systems circuitry 4120 and the supported communications protocols stack 4130; the Power Circuitry 4140 with notification mechanisms 4150, such as the LED Indicator; the Audio Circuitry 4160 and the Video and Imaging Circuitry 4170.

The Network Systems circuitry 4120 may include well-known circuitry for performing these functions, including but not limited an antenna system, an RF transceiver, one or more amplifiers, a tuner, one or more oscillators, a digital signal processor (DSP) 4180, a CODEC chipset as in 4160, a subscriber identity module (SIM) 4190 card, WiFi module 4220, Bluetooth module 4230, memory (such as primary memory and cache) 4200, secondary memory 4210, and so forth.

Peripheral interface 4020 may include the following peripherals and their modules: a Graphical +/Analog Interface 4280, which may be coupled to a Display Interface (LCD/LED/etc) 4260; Graphical +/Analog Interface 4280 may process requests to and from a joystick 4270 device; the touch pad module 4240; keypad or keyboard module 4250, or another such device.

Figure 16C:
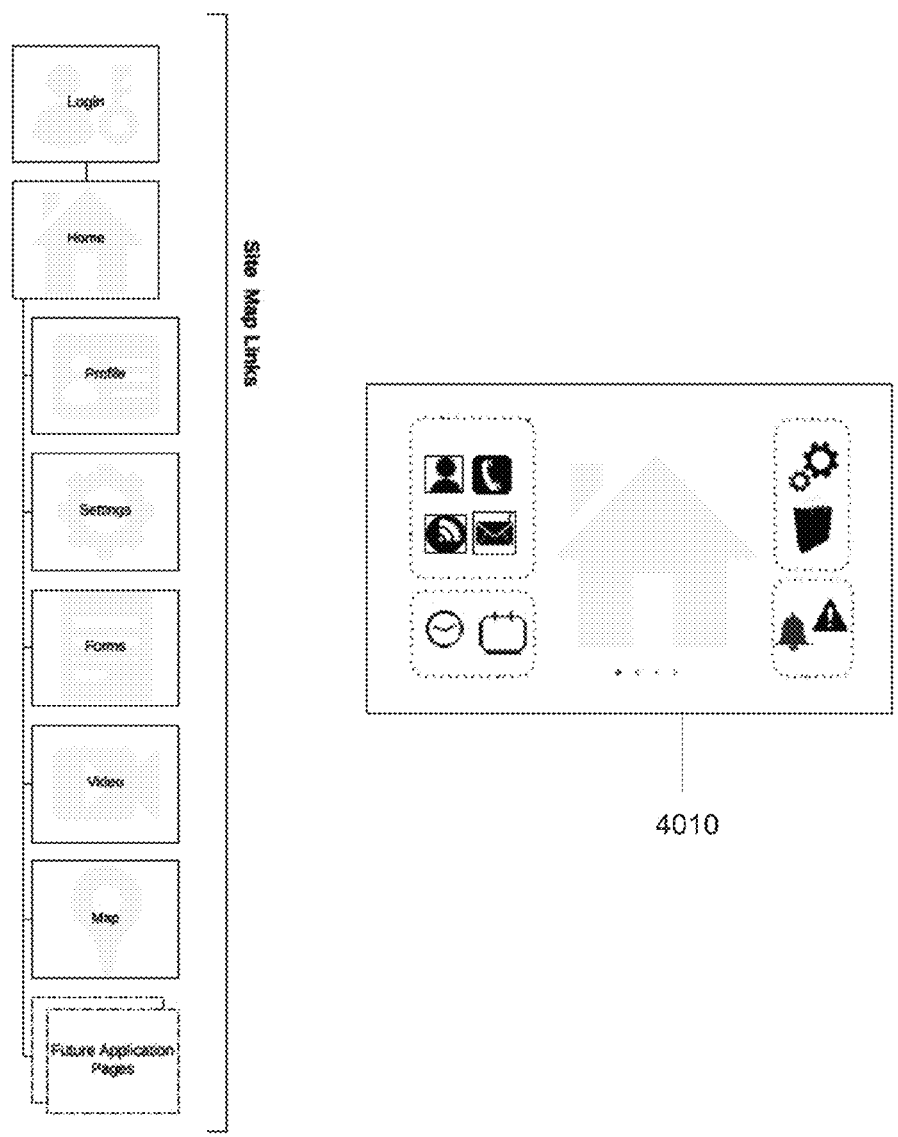

FIG. 16C is a representation of one embodiment of the user interface 4010 programmed elements of the mobility device displayed to user over a display medium.

Elements such as time and date element, notifications element, alerts element, communications element (contacts, social media, live messenger and 3rd party communication solutions, email, dialing, etc), application store element for downloading and/or integrating with 3rd party software, settings element, site map link elements, and other might be exposed to user of the mobility device after proper access controls have been successfully executed (identification, authentication, authorization, access approval, audit). Additionally, a GPS and a weather tracking element might be provided. Controls for speed, seat position, maneuverability, auto pilot, safety parameters, other controls and elements and/or their parameters might be configurable via the settings element. Regardless of the API level exposure of the elements to a user, a user can hide, remove, customize visual presentation of the elements. The settings element may also be utilized for creating rules and activity profiles for the activity manager. The settings element might also be used by user for setting security and data acquisition or collection permissions to limit data access to other user and application components of the distributed system. A different set of elements might be exposed to another user and type of user by the API, for example, to a physician.

Figure 17:
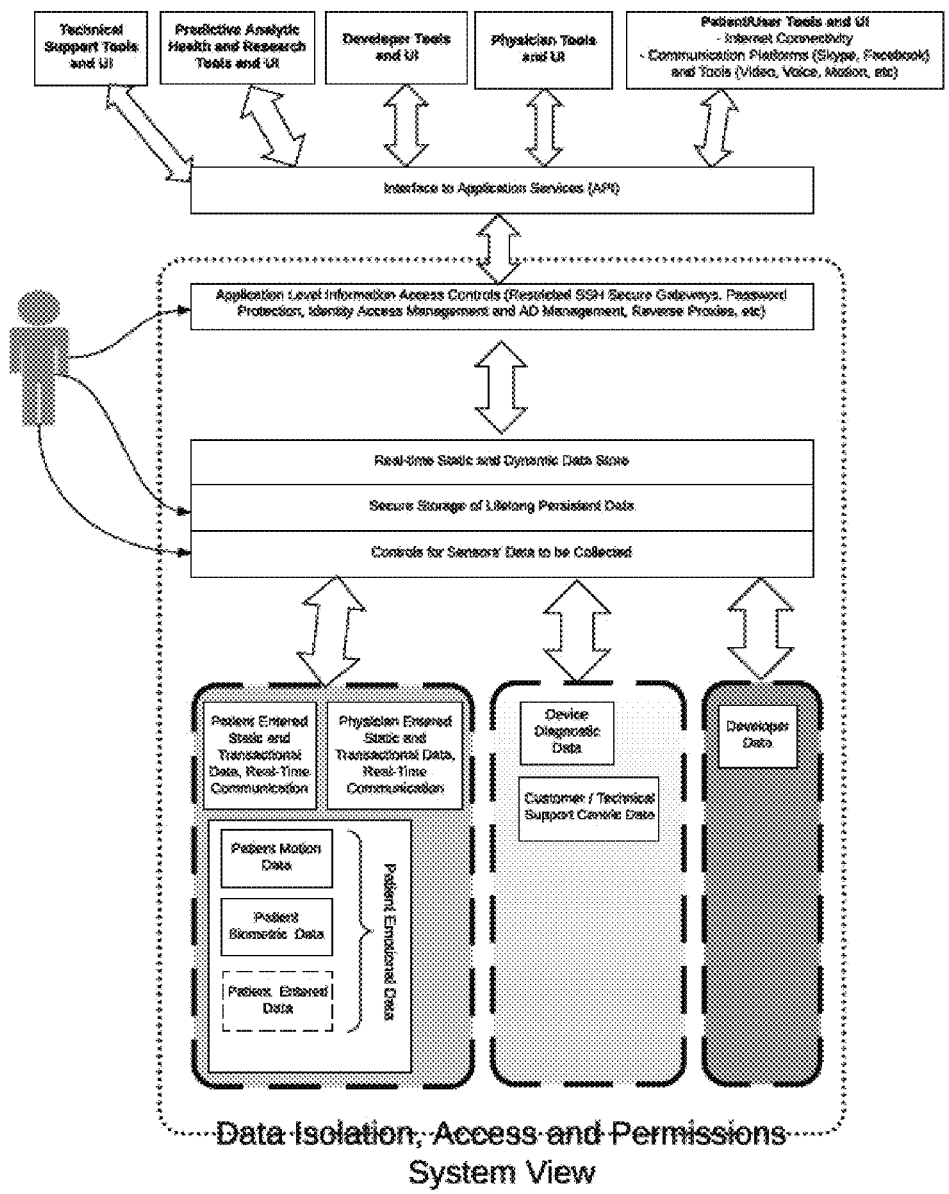
FIG. 17 illustrates an application platform for data utilization and security layers according to some embodiments of the disclosed technology.

FIG. 17 is a high-level view of data utilization and security layers of the application platform from a user perspective.

Figure 18:
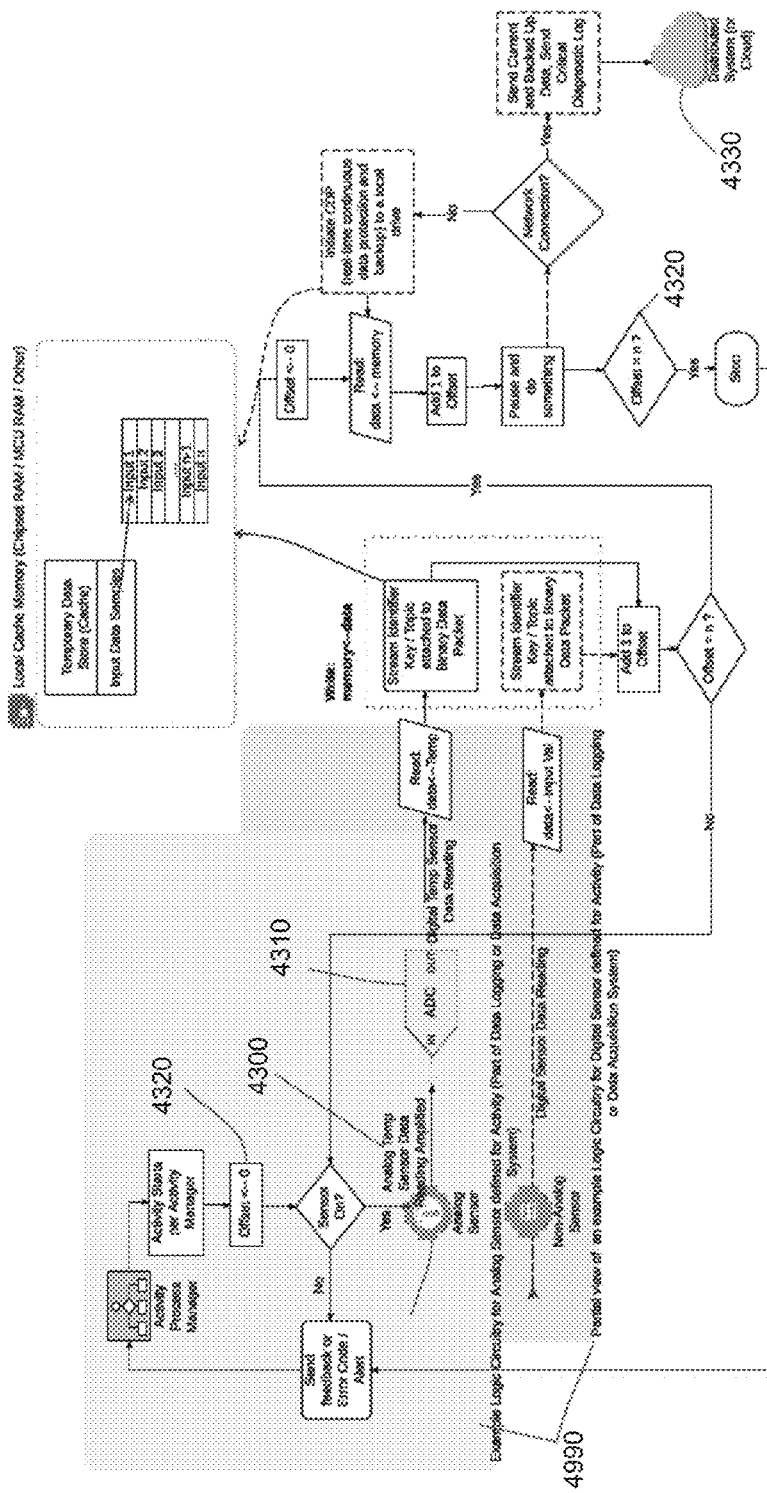
FIG. 18 illustrates a data acquisition system and a processing system according to some embodiments of the disclosed technology.

FIG. 18 is an illustrative example of a possible configuration of a data acquisition system (DAQ) and a processing system of the mobility device. The data logging system or a data acquisition system (DAQ) 4990 may be considered as function of the computer interface 4040, as it routes and manages data and access to and from the input/output devices.

The typical components of a data acquisition system might include: sensors 4100, 4110 which can be either analog or non-analog, and is a type of a transducer (it senses the physical parameters, such as temperature, pressure, etc. and transforms these into electrical parameters, such as voltage, current, resistance), signal conditioning circuitry 5000 to amplify, attenuate, compensate, filter or else condition a signal from transducer or sensor before it is sent to a measurement hardware (an ADC) such as is done by an amplifier; analog-to-digital (ADC) converter(s) 4310, and sometimes digital-to-analog (DAC) converter(s), for example, to complete a dependency function for a given circuit logic; actuator(s), which are a type of a transducer and carry out the mechanical action or decision made by the control system usually sent as an electrical signal to the actuator; a computing component or a computer which supplies the DAQ with processing component 4050, 4060, a system clock 4090, memory 4200, 4210 and space to store data, and a bus 4120, to transfer data between the components; and software, which allows you to configure data acquisition parameters between the hardware components and computing device such as intelligence system 4000 (i.e. configuring sampling rate of your board, and acquire a predefined amount of data, etc) referred to as driver software, and provides a user friendly front-end to define and otherwise manage these configurations; additionally, some implementation of a counter/timer circuitry 5020 is useful and implemented for many applications, such as counting occurrences of a digital signal, which uses resolution to define the number of bits the counter uses to count up (the higher the resolution, the higher the counter can count), and the frequency to determine how capable the counter is of detecting higher frequency and thus generate higher frequency pulses on the output, which also depends on the clock frequency.

Referring now to FIG. 18, in one embodiment mobility device is incorporated within or constitutes as part of a supporting distributed system 4330 for its digital communications and processing, including, but not limited to, the following functionalities: An implementation of a data stream management system (DSMS) 4340; data producers 4350 that send the acquired data 4360 from the mobility device, both live and stored, and including any error logs to the distributed system 4330; data consumers 4370 which can be applications, engines, servers, and controllers of the distributed system; working storage 4380; real-time processing 4390; real-time database system 4400; persistent storage 4410; archive storage 4420 and long term storage; application and mapping platform 4430 to control application (and/or operating system) configurations; software deployment tools and platform 4440; reporting platform 4450; analysis/machine learning systems 4460; restricted gateways 4470; client and application user devices 4480; and load balancing 4490 for balancing the load of data transfers and requests to and from servers.

Referring now to FIGS. 16A-16B, in one preferred embodiment the mobility device has intelligence.

As a non-limiting example, FIG. 16B illustrates one embodiment of the components of a computer interface 4040 responsible for the intelligence of the mobility device.

"Distributed system" represents a set of the computing components working together to complete a method or a set of methods of the disclosure. Whereas it generally refers to a global picture of all the "computing components" networking together to effectuate a purpose or a method of the disclosure, a "computing device" represents a set and configuration of the "computing components" which might be housed on a single mobility device and is thus compact or contained to that mobility device. Such a "computing device" sometimes employs the components of the distributed system and its infrastructure to effectuate a purpose or method of the disclosure.

Such a computing interface 4040 may also encompass a mobile device coupled to the computing interface 4040. In this configuration, the computing device may utilize input/output components of the mobile device, such as a display, LCD controller, buttons, audio and RF circuitry, etc., on the mobile device. The choice of using one component over another, where this choice exists, can, in some embodiments, be made autonomously, for example, by comparing respectable properties of both components against each other, or manually by a user. In one embodiment, a mounting can be provided by the mobility device to mount a mobile device to the computer interface 4040 of the mobility device.

"Infrastructure" refers to information technology, the physical hardware used to interconnect computers and users, transmission media, including telephone lines, cable television lines, and satellites and antennas, and also the routers, aggregators, repeaters, computers, network devices, applications, and other devices that control transmission paths, software used to send, receive, and manage the signals that are transmitted, and everything, both hardware and software, that supports the flow and processing of information. In this way, but without limitation, Infrastructure as a Service (IaaS) can also be a part of the infrastructure as pertains to the disclosure.

Architecture, as used herein, refers to the Logical View of the infrastructure and of the distributed system to enable the processes required for the scenarios or use cases to be possible as methods or purposes of the disclosure. The architecture is built to provide the best efficiency. The architecture can change and evolve as technology evolves and standards change.

As used herein, "event" is defined as a change in a state. An event is anything that happens, or is contemplated as happening, which usually is communicated in a message form or event form relating to infrastructure or software, or another data traversing the infrastructure. An event can include a time stamp, and a name for the entity that is changing state.

In one embodiment, the system tracks a change in state ("event") of a predefined parameter value or a combination of parameter values, or a range of values, as relative to some predefined original state as defined within the scope of the data collected, passed or previously stored, and as these changes are recognized by the computing device.

As a non-limiting example consider a change in a state of the device hardware internal temperature, where temperature value is the parameter value, or a variable which is being monitored by the system. Any change in the value of the variable signifies an event, also synonymous to a 'change in state'—of this variable or parameter. The ability and the effectiveness of the computing device or computer or of the distributed system to recognize a change in a state of a variable depends on the programmed logic that is responsible for the monitoring, but also on the hardware, firmware, and network limitations of the components of the device or system, such as sensor(s), or ADC and DAC components, if participating in the process, etc. In this way, an event is recognized and is handled as part of the processing logic existing within the distributed system or a computing device. As a non-limiting example, events can be generated autonomously, such as when a prior event or a combination of prior events occurring triggers the next event(s), or they can also be generated manually via input from a user. State changes may be filtered and/or 'logged' according to programmed rules, such as a running script. A log may then be processed or analyzed by a computing device autonomously or checked manually by a user, such as by opening a log file and reviewing. As a non-limiting example, a log file is useful in the case of troubleshooting a mobility device component by technical support personnel or by a manufacturer.

In one embodiment, consider that a computing device tracks the movement of a mobility device user about a confined space, such as a room, based on a pre-defined reference point, taken as an x, y, z value for a duration of time defined as a static variable t. Based on previously collected and stored data, it may have been determined that the user on average moves x amount of feet in x direction, y amount in y direction, and stays in the same vertical position z during the interval t between certain hours of the day. An event can then be defined as a significant change in the movement of the user in either one of the directions per time duration t. As example, consider that the user has decided to change his vertical position. The new value and the vertical displacement can be identified by the computer interface 4040, the controller 4060, or by the distributed system 4330 as two distinct events and state changes. These events may in turn prompt other events or processes to begin, or they can each prompt a combination of a number of events and processes. One of the events, for example, will cause a new value added to the collection of earlier collected or stored data for the z parameter. This will cause a new z mean displacement value to be derived and stored. Additionally, the computing device can use either of the results to send to a physician as a notification or an alert message and/or it can prompt the user of the mobility device via a display or as an audible message, or both for input.

A "computer interface" is a shared boundary across which two separate components of a computer or a computing system exchange information. The exchange can be between software, computer hardware, peripheral devices, humans and combinations of these. A "computer interface" and a "user interface" can be used synonymously. However, with a "user interface", it is assumed, unless otherwise stated, that a display 4260 and a touch-pad 4240 are parts of that interface.

A display 4260 or a touch-pad 4240 need not be touch-sensitive or incorporate multi-touch technology. It is assumed that when required to do so, a user is enabled to communicate with the systems (computing device, the mobility device and the distributed system) by ways of other I/O devices and suitable to the systems user interfacing technologies. This can be regarded part of the customization of the computer interface layer.

A "user interface" is the means by which the user and a computer system interact, in particular the use of input devices and software. User interfaces may include a computer with a monitor (or a laptop, a tablet, a mobile device), a keyboard, a keypad, a touchpad, a mouse, a joystick or other input devices performing a similar function.

As used herein, a "display" or screen can include a surface, medium, material, graphic representation or any other means that allow a visual presentation of data. Access to data could be over or partially over other forms of computing and/or communications networks. A user may access a web-browser application, e.g., to gain access to other applications and to the data served over the Internet, or to other content located on a web-site.

In this document "intelligence" generally refers to any automated functionality such as of the computer interface 4040 and controller 4060 that can control the device with both hands-on and hands-off systems, and that can integrate any assistive technology, connectivity, sensors, communications and alert systems; such as resulting and actionable data from performing statistical analysis on the collected information to develop observational, inferential, experimental, predictive and actionable results. Such automated functionality is usually, but without limitation, enacted by algorithms, conditional statements, and the like, as part of software code which can be embedded, developed or otherwise provided to the distributed system.

A sensor network is composed of a large number of sensor nodes which are densely deployed either inside the phenomenon or very close to it. Each node is connected to one (or sometimes several) sensors. The position of sensor nodes need not be engineered or pre-determined. Sensor network protocols and algorithms must possess self-organizing capabilities. Each such sensor network node has typically several parts: a radio transceiver with an internal antenna or connection to an external antenna, a microcontroller, an electronic circuit for interfacing with the sensors and an energy source, usually a battery or an embedded form of energy harvesting. Thus defined, a mobility device can carry a sensor network either wirelessly connected or embedded in some way with the computing of the mobility device.

When speaking of data in terms of the Internet of Things (IoT) technology and M2M communication (machine-to-machine) and their scope, it can be appreciated by those skilled in the art, that generally low latency and efficiency of how real-time data is being collected, processed, and integrated with other real-time or stored data is of concern to extract real-time results which can further be consumed by applications, further processing and integration, or displayed to users to improve understanding of how different data are related and to use that knowledge to extract further benefits.

Virtually all computers today, including embedded computers, mobile devices (cell phones, tablets, laptops etc), personal computers, servers, and other computing systems only understand digital data. Digital data is therefore machine readable. It is a discrete, discontinuous representation of information. Real-world or analog information can also be represented as digital data. Analog information is transformed into machine readable or a digital form by the electronics hardware such as ADC (analog-to-digital converter).

A single data stream can be defined as a continuous flow of entity state and state changes (such as measured by a sensor). A data stream can thus be interpreted as real-time information about an entity when given context, such as provided by logic from a query performed on the data, possibly involving another metric, which can in turn be an outcome of a previous query and/or computation performed on an older set of data regarding the same entity.

A mobile device can include an application for executing the methods of the present disclosure.

The computing device can include a display 4260 that can be a touch sensitive display. The touch-sensitive display is sometimes called a "touch screen" for convenience, and may also be known as or called a touch-sensitive display system. The computing device may include a memory (which may include one or more computer readable storage mediums), a memory controller, one or more processing units (CPU/MPU), a peripherals interface, Network Systems circuitry, including but not limited to RF circuitry, audio circuitry, a speaker, a microphone, an input/output (I/O) subsystem, other input or control devices, and an external port.

The mobile computing device may include one or more optical sensors. These components may communicate over one or more communication buses or signal lines.

It should be appreciated that the intelligence system 4000 is only one example of a computing integral to the mobility device, and that the computing device may have more or fewer components than shown in FIGS. 16A-16B, may combine fewer or more components, or a may have a different configuration or arrangement of the components. The various components may be implemented in hardware, firmware, software, or a combination of hardware and software, including one or more signal processing and/or application specific integrated circuits.

Memory 4200, 4210 may include high-speed random access memory and may also include non-volatile memory, such as one or more magnetic disk storage devices, flash memory devices, or other non-volatile solid-state memory devices. Access to memory by other components of the computing device, such as the CPU and the peripherals interface, may be controlled by the memory controller 2030.

The peripherals interface 4020 couples the input and output peripherals of the device to the CPU 4050, 4060 and the memory 4200, 4210. The one or more processors run or execute various software programs and/or sets of instructions stored in memory to perform various functions for the computing device and to process data.

In some embodiments, the peripherals interface 4020, the CPU 4050, 4060, and the memory controller 4030 may be implemented on a single chip, such as a chipset 4060. In some other embodiments, they may be implemented on separate chips.

The Network System circuitry 4120 receives and sends signals, including but not limited to RF, also called electromagnetic signals. The Network System circuitry 4120 converts electrical signals to/from electromagnetic signals and communicates with communications networks and other communications devices via the electromagnetic signals.

The Network Systems circuitry 4120 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The Network Systems circuitry may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication.

The wireless communication may use any of a plurality of communications standards, protocols and technologies, including but not limited to Global System for Mobile Communications (GSM), Enhanced Data GSM Environment (EDGE), high-speed downlink packet access (HS-DPA), wideband code division multiple access (W-CDMA), code division multiple access (CDMA), time division multiple access (TDMA), BLUETOOTH®, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP), instant messaging (e.g., extensible messaging and presence protocol (XMPP), Session Initiation Protocol for Instant Messaging and Presence Leveraging Extensions (SIMPLE), and/or Instant Messaging and Presence Service (IMPS), and/or Short Message Service (SMS), or any other suitable communication protocol.

The audio circuitry 4160 including the speaker and the microphone can provide an audio interface between the mobility device and the mobile computing device. The audio circuitry receives audio data from the peripherals interface, converts the audio data to an electrical signal, and transmits the electrical signal to the speaker. The speaker converts the electrical signal to human-audible sound waves. The audio circuitry also receives electrical signals converted by the microphone from sound waves. The audio circuitry converts the electrical signal to audio data and transmits the audio data to the peripherals interface for processing. Audio data may be retrieved from and/or transmitted to memory and/or to the Network Systems circuitry 4120 by the peripherals interface 4020.

In one embodiment, referring also to FIG. 16B, the audio circuitry 4160 also includes a headset jack. The headset jack provides an interface between the audio circuitry and removable audio input/output peripherals, such as output-only headphones or a headset with both output (e.g., a headphone for one or both ears) and input (e.g., a microphone).

The I/O subsystem couples input/output peripherals on the mobile computing device, such as the touch screen and other input/control devices, to the peripherals interface. The I/O subsystem may include a display controller and one or more input controllers for other input or control devices.

The one or more input controllers receive/send electrical signals from/to other input or control devices. The other input/control devices may include physical buttons (e.g., push buttons, rocker buttons, etc.), dials, slider switches, and joysticks, click wheels, and so forth.

In some alternate embodiments, input controller(s) may be coupled to any (or none) of the following: a keyboard, infrared port, USB port, and a pointer device such as a mouse.

The one or more buttons may include an up/down button for volume control of the speaker and/or the microphone. The one or more buttons may include a push button. A quick press of the push button may disengage a lock of the touch screen or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety.

A longer press of the push button may turn power to the computing device on or off. The mobility device user or designee can customize a functionality of one or more of the buttons. The touch screen is used to implement virtual or soft buttons and one or more soft keyboards.

In one embodiment, a mobility device has a computing ability to identify, collect, update, encrypt and decrypt, format the data, log, send and receive, or purge data, as needed, by utilizing the embedded technology and the computing device components of the mobility device.

In one embodiment a mobility device has a mobile device residing on a mobility device and coupled to a computing device (intelligence system) 2000 of the mobility device.

In one embodiment, an operating system (OS) and platform independent user interface layer displays data to the user by displaying it on the display of a mobile device coupled to a computing device, on the display screen of the computer interface 4040 of the mobility device, or on another client device in communication with the distributed system.

In one embodiment, mobility device provides an OS and Platform independent user interface (programmed elements can be served over a display medium).

A joystick 4270, touch pad 4240, keypad 4250, and a touch sensitive display (or multi-touch) 4260, in one embodiment, can all be referred to as the user interface 4010 (tangible) components. These may be coupled as external devices, each within their module, or these can also be integrated into a mobile device mounted onto computer interface 4040, or another engine (or hard shell) coupled to computer interface 4040. Alternatively, the computer interface 4040 might supply the native 4010 devices. In either case, these provide a user an ability to interact with the displayed elements, and with the computing device.

In one embodiment, an OS and platform independent user interface layer enables a user to interact with the distributed system 4330.

This is facilitated in one possible embodiment, but in no way as limitation of other possible combinations, by use of a present touch-sensitive display, a touchpad or a joystick coupled to the display controller, displaying in some scenarios an onscreen keyboard, or in combination with an audio circuitry, to perform conversion of data from analog audio signal to electrical to digital, and then to match the data received to existing patterns representing words and letters of the alphabet, otherwise interpretable as human language, or commands tied to program code and eliciting an event or a series of events from the system.

In one embodiment, a mobility device has an interactive computer interface.

Referring still to FIGS. 16A-16B, it should be appreciated that a computer interface 4040 may include any human-machine interaction technologically made available, which as a non-limiting example can be via touch, motion, voice, another input device, such as a keypad, keyboard, mouse or a joystick, or a combination of such devices, where all the different combinations are too many and it is not imperative to list or represent them here.

In one embodiment, assistive technology is provided for the visually impaired, in that the device describes using voice cues or voice indications what is surrounding the device, to be able to guide the visually impaired.

Audio circuitry is utilized to perform conversion of data from digital to electrical signals and then further converted to analog audio signal, possibly via some signal conditioning to enhance the audio signal. For example, text suggestions tied to programmed events will be transposed this way from digital text to an analog sound for a user to interpret as human language.

In one embodiment, a mobility device has a customizable computer interface layer. This refers to that the mobility device may include any combination of the add-on and assistive technology and is not limited to any single configuration. Additionally, it can refer to the elements on a user display screen as well as their formatting and placement on the page, or available attribute and properties configurations.

In one embodiment, a mobility device has suitable architecture for integrating various data types made available to it. Because a mobility device is considered to be customizable, and an infrastructure can support more than one mobility device, it is assumed that the distributed system similarly has a suitable architecture to effect purposes and methods of the disclosed technology, which should include the integration of various data types made available to it.

As a non-limiting example, in the case that a data type or data structure is not recognized by the infrastructure and distributed system, it is assumed that the system is able to cope with these situations, for example, and without limitation, by storing an erroneous data in a log file and alerting the administrating user of the infrastructure and of the distributed system, for example, by sending a message regarding the event, or an "event message". It is also assumed that the infrastructure can change and adjust to accept and recognize new data types and data structures; for example, error logs are reviewed by an administrating user. Program code is later adjusted to accept a new data structure or data type and the like.

A data logger is synonymous to a data acquisition system. The data logger stores the data for a period of time before sending it in a pre-defined batch size to a computer, a computing device, or a server which will process or analyze it.

In general a data logger device can include an internal microprocessor (MPU), data storing, data transducer (ADC, DAC, etc.), and one or more sensors.

Data loggers can be deployed indoors, outdoors, and underwater, and can record data for up to months at a time, unattended. A data logger may be a single-unit microcontroller (MCU), such as a stand-alone device with internal sensors and which fits in the palm of a hand, or it may be a multi-channel data collection instrument equipped with one or more external sensors, or inputs for multiple sensors.

Thus described, it is entirely conceivable that a computing device residing on the mobility device can support either in part, such as possible, yet not required in a distributed system, or house entirely a data acquisition system which can additionally communicate and log data from supplementary instruments, sensors, MCUs, or other such input devices.

As an illustrative example only, consider a data acquisition system encompassing two sensors: an analog and a digital sensor. As a sensor takes a reading, the data is sent through a cable or wireless link to data logger.

The temperature sensor is set as an analogue input.

The 'Read: input' symbol reads the analogue value on a pin and saves it to a variable; in this case called 'data'.

The write output has been set up to write the variable data into the short-term (data) memory of the microcontroller (MCU), a part of the data acquisition system.

The offset value ensures the data is stored in separate memory locations. In this case, the first sample goes into location zero, the second sample into location 1, and so on up to n. So that in this flowchart n samples are taken and stored. The data can then be read from short-term memory and stored in a variable using the read input.

This value can then be used to control outputs or to be displayed (via a reporting web or local application user interface layer). It could also be downloaded for any purpose to another drive (such as for data back-up or to be shared to another application for internal processing, such as analysis processes performed on the data), or it could be shared to other users via email or another type of communication.

As a non-limiting example only, a data stream may be illustrated by FIG. 18.

A sensor captures real-time data which is sent as packets of digital data to a computing device, such as a storage medium, which can be a local or an externally hosted medium connected to the sensor technology via an active communication link including but not limited to: ex: Wi-Fi, WiFi-Direct, Bluetooth, USB and the like.

In one embodiment, referring to FIG. 18, a computing device is listening to the real-time input data and processes the data queues according to any number of scripts which are executed for proper processing of the data, such as appending a timestamp to the data, appending an event ID or another identifying key to the data, filtering the data based on predefined parameters, performing error checking at the time of data capture or at the time of data release to another accessing device, parsing the data and performing any other actions defined for processing of that data.

As a non-limiting example, FIG. 18 is only as an example of one possible programmed logic for processing of data, but other configurations are possible. There may be any combination of scripts performing similar or other types of logic on the data and incorporating a variety of hardware, firmware, and software components made available. Additionally, the local storage or memory is depicted as a CDP process.

As a non-limiting example, a computing system, and its distributed system should be able to further manage and process acquired data. Before this is possible, the data typically needs to be massaged into some workable format which follows a defined set of syntax and semantics rules. Once this is done, the distributed system components which are to perform processes on these data (including systems in the cloud) are able to understand and process it further.

As a non-limiting example, data can be syntactically analyzed and inserted into a type of a predefined array for that data type and then loaded into a temporary memory table. This data can sit within the local temporary data table until it is uploaded to the database 'in the cloud', after which it is purged from the local data table to free space for the new data to be logged in similar way.

In one embodiment, programmed logic is encapsulated by a set of scripts or code triggered on an event or a sequence of events. Any computation performed on the stored data is part of that logic. Additional processes can be performed asynchronously and independent of this logic or concurrently as part(s) of this logic.

In one embodiment, a system is programmed to check for an existing connection between communicating nodes on the local computing device and the computing device 'in the cloud' prior to attempting a data upload. If the system establishes that there is a working connection between the devices, the local device, possibly in conjunction with other application or firmware, will start to send real-time data to a computing device 'in the cloud', such as distributed data warehouse, an ELT (Extract, Load, Transform) or an ETL solution.

In one embodiment, a system may be able to also send any critical logged information stored locally on a mobility device in a computing device's temporary memory or storage.

For example, a subset of data is stored locally if the system determines that there is no working network available for immediate data transfer.

As a non-limiting example, some parts of the distributed system and infrastructure can be hosted remotely, either "in the cloud", for example, by a third party provider, (Amazon Web Services, Orange, IBM, etc) or set up and/or owned by the company on a remotely located and managed server.

FIG. 18 illustrates one embodiment of a distributed system 4230 logical high level schema or architecture and infrastructure, where the said elements work together to perform methods and functionality of the disclosed technology and of a mobility device.

A distributed system typically might include a type of an operational platform, which includes the networking gear (hardware and firmware), servers (application servers 4430, database servers 4400, etc), operating systems installed onto the servers (Linux, Unix, Windows Server version, etc) baseline configurations for server types (server images from templates, deployment and configuration scripts, other), and some monitoring of the operational status (disk, memory, cpu, etc.) such as SaaS, or developed and/or locally installed software packages, or some other solution; a deployment and an application management system 4440, to get the application components onto servers and control these application components. Additionally, some implementation of a configuration management system maintain commonality regarding the operating systems and application versions distributed and residing on the different types of servers (for example, an application configuration system may be tied to the deployment system and publishes or pushes new configuration sets to an application layer of the operational platform). In general, operating systems help to facilitate roles for servers. Thus one operating system might work well for a Web server, but a different operating system will work better for serving files (i.e. file server), to server an application code (application server), to store, update and retrieve data (database server), or for user management, security, access and routing (network server) etc.

A distributed system 4230 might be one or more servers, as long as these are accessible to the intelligence system 4000 over the network and are able to extend the functionality or method of a single mobility device's native intelligence. Thus, it is entirely possible that a single physical server's CPU, memory, Network Systems circuitry, and any other native components and technology might, at least in some embodiments, provide a working distributed system platform for the disclosed technology.

Figure 19:
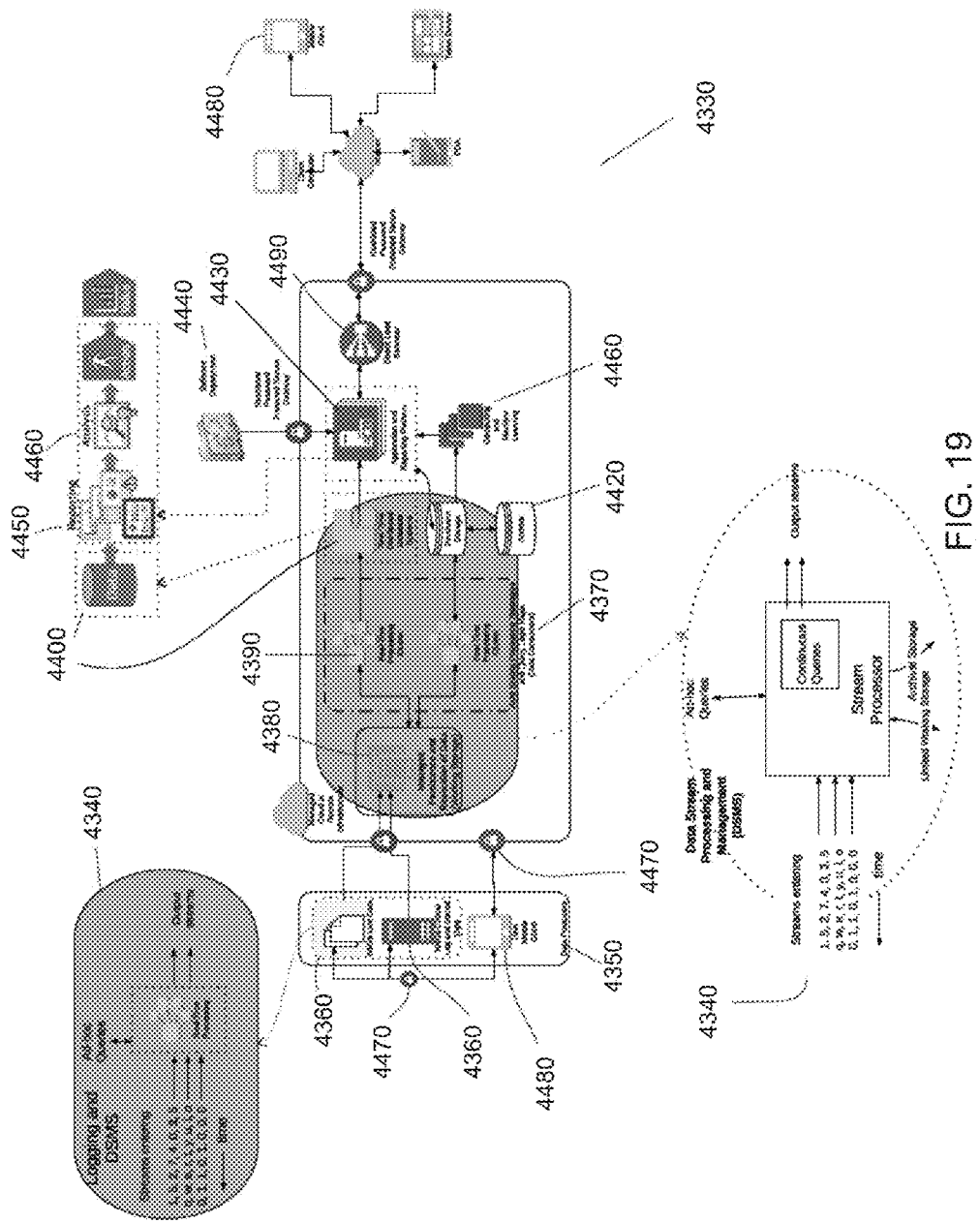
FIG. 19 illustrates a global view of a distributed system of the disclosed technology according to some embodiments.

Furthermore, referring still to FIGS. 18, 19, a data stream is usually managed by a Data Stream Management System (DSMS). While a data acquisition system or a data logger is generally responsible for the acquisition of the data, the DSMS is responsible for the organization and organized processing of stream data.

The main difference between a DSMS and a traditional relational Database Management Systems (DBMS) is that a DSMS supports a continuous query (CQ) or a standing query, while a traditional DBMS does not. In a traditional DBMS, the queries are one-time queries ran against a state of data taken at some snapshot of time. When a CQ is introduced into a DSMS, such as ad-hoc, by a user, it can continuously execute as long as data is pushed to the query and as long as the query is not removed from the system.

As data is being collected by a sensor and pushed to the processing components of a distributed system or a DSMS 4500, a continuously running query within a DSMS can be performed against input data to identify and store only the data that is in some way more meaningful than all the other data. In this way it keeps a summary of data and retains only a synopsis. This can significantly minimize storage requirements, and can be an effective approach depending on a use case For example:
SELECT sample
FROM sensors
WHERE temp>MAXTEMP In data-stream management system (DSMS) 4500 any number of streams can enter the system. Each stream can provide data at its own schedule and at different rates with different data types.

A data consumer, in addition to filtering for data with some identifying properties such as an entity identifier key, might impose a limit on the interval of data to be listened based on a timestamp, the number of samples in a tuple, or another metric.

To process multiple queries efficiently, the sensor database management system might also implement scheduling technique for query execution and share the results among queries and data consumers.

Additionally, some or all raw data can still be stored for later access or aggregation, etc.

Any query or resulting data can in some embodiments be stored in a non-volatile and a non-transient way in storage (ex: hard drive, optical disk, USB drive, solid state drive, etc) or temporarily in the memory of a computing device (ex: RAM). Data can also be replicated in part or in whole to any device within the network. It can be hosted, further processed and served to other components of the system, for example when multiple processes need to be performed on the data and the results stored or further shared across networks for different purposes, which may include updating of stored variable data and further processing, or simply representing the results as graphs or in other format on a client device display medium when user views the reporting dashboard.

In one embodiment, statistical analysis is performed on the data while live reporting.

The raw data which has not been processed can be archived or stored in another block storage for much more grain-level and intensive processing and analytics. The resulting data can be used for machine learning such as in experimental, predictive and inferential analytics. In the future, the new algorithms developed by analyzing this data can be implemented as new data stream topologies.

Some or all analysis of data can be performed by the computing of the mobility device alone. However, it should be appreciated that the components remotely located and the associated additional Network Systems can be used as additional resources to augment the architecture and the computing of the mobile device, but are not necessarily required in all the possible embodiments.

In one embodiment, a mobility device is coupled to a system of computing components that are not native to the mobility device and not located in the proximity of the mobility device, and thus can be considered remote. In such an embodiment, by those skilled in the subject matter, it will be appreciated, without imposing limitation on other embodiments, that these components may be hosted 'in the cloud'. It should be understood also that such a system may include one or more computing components which at least sometimes work together to effectuate a purpose or method(s) of the disclosure. The distributed system can therefore, in one embodiment, be dynamic and continuously changing to apportion the required resources as and when they are needed.

FIG. 19 represents a schematic and logical diagram of one possible embodiment of a distributed system which includes remote infrastructure to perform methods of the disclosure. Such a remote infrastructure can also be a cloud services infrastructure that can be utilized with the present disclosure.

Cloud Services

FIG. 19 can describe in one configuration the data management by a remote system of computing components, such as cloud services, which might include IaaS, PaaS, and SaaS. Once a working network connection is established, and recognized by the intelligence system 4000 on a mobility device data residing or collected by the data acquisition system on the computing device can be shared (pushed or pulled) to the cloud. It should be appreciated, that sometimes, data might also be traveling to a mobility device from the distributed system.

In some embodiments, all or parts of the computing described further can also be housed on a mobility device.

In one embodiment all the streaming data and also the critical data logged during the time of no working network connection are sent to the systems 'in the cloud' according to programmed logic. Additionally, as part of the existing programmed logic between the local system and the system 'in the cloud' an identifier values such as from an identifier monitor are attached to each data sample to identify the pre-defined topology or query map for any data construct sent to and received by the system 'in the cloud' and also to identify the local device as part of the authentication and security processes of the system.

In one embodiment a real-time processing cluster enacts predefined programmed parsing, formatting, massaging, and other processes on each data abstract before it is being stored in a real-time database system.

In one embodiment another processing cluster can push the data to a persistent storage where much more complex computing takes place and historical data is compared, as well as new algorithms are defined and imposed on the data. The results are also stored in a system's store.

In one embodiment a load balancer equally distributes requests to the data within the reporting platforms and to the application as well as acts as a firewall for external requests, masking the internal components and protecting from unauthorized access and tampering of the program and stored data, as well as any other elements existing 'in the cloud' as part of the system.

In one embodiment requests to the application code and reporting platform or stored data can come from client devices running the client application software which provides interface layers and controls specific to the type of the interface used to access the data.

As shown, the cloud services encompasses web applications, computing devices, personal computer and/or laptops and social networks, such as, Twitter®.

It will be appreciated that other social networks can be included in the cloud services and Twitter® has been given as a specific example. Therefore, every component forms part of the cloud services which comprises servers, applications and mobility device users.

The cloud can provide the mobility device user access to services with the utilization and allocation of remotely located hardware and software resource(s). The system can concurrently service requests from several users without participant perception of degraded computing performance as compared to conventional techniques and where computational tasks can be performed upon a mobility device user or a server within a proprietary intranet.

The cloud services provider supports a collection of hardware and/or software resources. The hardware and/or software resources can be maintained by an off-premises party, and the resources can be accessed and utilized by identified participants over Network System. Resources provided by the cloud services provider can be centrally located and/or distributed at various geographic locations. For example, the cloud services provider can include any number of data center machines that provide resources. The data center machines can be utilized for storing/retrieving data, effectuating computational tasks, rendering graphical outputs, routing data, and so forth.

In one embodiment, the cloud is used for the interfacing with a mobility device as part of the distributed system.

According then to an illustration in FIG. 19, the cloud services provider can provide any number of resources such as data storage services, computational services, word processing services, electronic mail services, presentation services, spreadsheet services, gaming services, web syndication services (e.g., subscribing to a RSS feed), and any other services or applications that are conventionally associated with personal computers and/or local servers.

Further, utilization of any number of the cloud service providers similar to the cloud services provider is contemplated. According to an illustration, disparate cloud services providers can be maintained by differing off-premise parties and a participant can employ, concurrently, at different times, and the like, all or a subset of the cloud services providers.

By leveraging resources supported by the cloud services provider, limitations commonly encountered with respect to hardware associated with mobility device users and servers within proprietary intranets can be mitigated.

Off-premises parties or Network System administrators of servers within proprietary intranets can maintain, troubleshoot, replace and update the hardware resources.

Further, for example, lengthy downtimes can be mitigated by the cloud services provider utilizing redundant resources; thus, if a subset of the resources are being updated or replaced, the remainder of the resources can be utilized to service requests from participants. According to this example, the resources can be modular in nature, and thus, resources can be added, removed, tested, modified, etc. while the remainder of the resources can support servicing participant requests.

Moreover, hardware resources supported by the cloud services provider can encounter fewer constraints with respect to storage, processing power, security, bandwidth, redundancy, graphical display rendering capabilities, etc. as compared to conventional hardware associated with mobility device users and servers within proprietary intranets.

The system can be associated with a mobility device that employs resources of the cloud services provider. Although one mobility device is depicted, it is to be appreciated that the system can include any number of mobility devices, and the plurality of mobility devices can concurrently utilize supported resources.

Resources can be shared amongst a plurality of mobility devices subscribing to the cloud services provider. According to an illustration (FIG. 19), one of the resources can be at least one central processing unit (CPU), where CPU cycles can be employed to effectuate computational tasks requested by the mobility device.

Pursuant to this illustration, the mobility device can be allocated a subset of an overall total number of CPU cycles, while the remainder of the CPU cycles can be allocated to disparate mobility device(s) (or other computing devices of the system). Additionally or alternatively, the subset of the overall total number of CPU cycles allocated to the mobility device can vary over time. Further, a number of CPU cycles can be purchased by the participant of the mobility device.

In accordance with another example, the resources can include data store(s) that can be employed by the mobility device to retain data. The participant employing the mobility device can have access to a portion of the data store(s) supported by the cloud services provider, while access can be denied to remaining portions of the data store(s) (e.g., the data store(s) can selectively mask memory based upon participant/device identity, permissions, and the like). It is contemplated that any additional types of resources can likewise be shared.

The cloud services provider can further include an interface component that can receive input(s) from the mobility device and/or enable transferring a response to such input(s) (as well as perform similar communications with any disparate mobility devices). According to an example, the input(s) can be request(s), data, executable program(s), etc. For instance, request(s) from the mobility device can relate to effectuating a computational task, storing/retrieving data, rendering a participant interface, and the like, via employing one or more resources. Further, the interface component can obtain and/or transmit data over a Network System connection. According to an illustration, executable code can be received and/or sent by the interface component over the Network System connection. Pursuant to another example, a participant (e.g. employing the mobility device) can issue commands via the interface component.

In one embodiment, the cloud services provider includes a dynamic allocation component that apportions resources, which as a non-limiting example can be hardware resources supported by the cloud services provider to process and respond to the input(s) (e.g., request(s), data, executable program(s), and the like), obtained from the mobility device.

Although the interface component is depicted as being separate from the dynamic allocation component, it is contemplated that the dynamic allocation component can include the interface component or a portion thereof. The interface component can provide various adaptors, connectors, channels, communication paths, etc., to enable interaction with the dynamic allocation component.

In one embodiment a system includes the cloud services provider that supports any number of resources (e.g., hardware, software, and firmware) that can be employed by the mobility device and/or disparate mobility device(s) not shown. The cloud services provider further comprises the interface component that receives resource utilization requests, including but not limited to requests to effectuate operations utilizing resources supported by the cloud services provider from the mobility device and the dynamic allocation component that partitions resources, including but not limited to, between participants, devices, computational tasks, and the like. Moreover, the dynamic allocation component can further include a participant state evaluator, an enhancement component and an auction component.

The mobility device user state evaluator can determine a state associated with a mobility device user and/or the mobility device employed by the user, where the state can relate to a set of properties. For instance, the mobility device user state evaluator can analyze explicit and/or implicit information obtained from the mobility device (e.g., via the interface component) and/or retrieved from memory associated with the mobility device and mobility device user in the cloud (e.g., preferences indicated in subscription data). State related data yielded by the mobility device user state evaluator can be utilized by the dynamic allocation component to tailor the apportionment of resources.

In one embodiment, the mobility device user state evaluator can consider characteristics of the mobility device, which can be used to apportion resources by the dynamic allocation component. For instance, the mobility device user state evaluator can identify that the mobility device is a mobile device with limited display area. Thus, the dynamic allocation component can employ this information to reduce resources utilized to render an image upon the mobility device since the cellular telephone may be unable to display a rich graphical interface.

Moreover, the enhancement component can facilitate increasing an allocation of resources for a particular participant and/or mobility device.

In one embodiment a system employs load balancing to optimize utilization of resources. The system includes the cloud services provider that communicates with the mobility device (and/or any disparate mobility device(s) and/or disparate cloud services provider(s)). The cloud services provider can include the interface component that transmits and/or receives data from the mobility device and the dynamic allocation component that allots resources. The dynamic allocation component can further comprise a load balancing component that optimizes utilization of resources.

In one embodiment, the load balancing component can monitor resources of the cloud services provider to detect failures. If a subset of the resources fails, the load balancing component can continue to optimize the remaining resources. Thus, if a portion of the total number of processors fails, the load balancing component can enable redistributing cycles associated with the non-failing processors.

In one embodiment a system archives and/or analyzes data utilizing the cloud services provider. The cloud services provider can include the interface component that enables communicating with the mobility device. Further, the cloud services provider comprises the dynamic allocation component that can apportion data retention resources, for example. Moreover, the cloud services provider can include an archive component and any number of data store(s). Access to and/or utilization of the archive component and/or the data store(s) by the mobility device (and/or any disparate mobility device(s)) can be controlled by the dynamic allocation component. The data store(s) can be centrally located and/or positioned at differing geographic locations. Further, the archive component can include a management component, a versioning component, a security component, a permission component, an aggregation component, and/or a restoration component.

The data store(s) can be, for example, either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable programmable ROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM). The data store(s) of the subject systems and methods is intended to comprise, without being limited to, these and any other suitable types of memory. In addition, it is to be appreciated that the data store(s) can be a server, a database, a hard drive, and the like.

The management component facilitates administering data retained in the data store(s). The management component can enable providing multi-tiered storage within the data store(s), for example. According to this example, unused data can be aged-out to slower disks and important data used more frequently can be moved to faster disks. Further, the management component can be utilized (e.g. by the mobility device) to organize, annotate, and otherwise reference content without making it local to the mobility device. Pursuant to an illustration, enormous video files can be tagged via utilizing a cell phone. Moreover, the management component enables the mobility device to bind metadata, which can be local to the mobility device, to file streams (e.g., retained in the data store(s)); the management component can enforce and maintain these bindings.

Additionally or alternatively, the management component—can allow for sharing data retained in the data store(s) with disparate participants and/or mobility devices. For example, fine-grained sharing can be supported by the management component.

The versioning component can enable retaining and/or tracking versions of data. For instance, the versioning component can identify a latest version of a document (regardless of a saved location within data store(s)).

The security component—limits availability of resources based on participant identity and/or authorization level. For instance, the security component can encrypt data transferred to the mobility device and/or decrypt data obtained from the mobility device. Moreover, the security component can certify and/or authenticate data retained by the archive component.

The permission component can enable a participant to assign arbitrary access permissions to various participants, groups of participants and/or all participants, such as users of the distributed system, or an application, such as third party application.

Further, the aggregation component assembles and/or analyzes collections of data. The aggregation component can seamlessly incorporate third party data into a particular participant's data.

The restoration component rolls back data retained by the archive component. For example, the restoration component can continuously record an environment associated with the cloud services provider. Further, the restoration component can playback the recording.

In one embodiment a mobility device generates intelligent on-time alerts or other programmed events (reminders, notifications, etc).

In one embodiment a mobility device collects user personal and health-type data.

In one embodiment a mobility device collects information about user's contacts (from social networks, history of messages, etc).

In one embodiment a mobility device collects performance and diagnostic data regarding the mobility device.

In one embodiment a mobility device or its distributed system, supporting infrastructure and its architecture enables real-time communication (RTC) between client devices, such as between a patient utilizing a display on his/her device and a physician's client device.

In one embodiment a mobility device enables communication between the mobility device user and people within a user's networks such as doctors, caretakers, family, friends as well as pets.

For example, a user can manage contacts via a displayed element on a user interface screen. A user can enter, update, remove or sync contact and contact details with $3^{rd}$ party applications.

In one embodiment a mobility device has an open-platform to integrate assistive technologies.

This is usually done by exposing a set of API libraries to an application layer and providing access to users or groups.

FIG. 19 discloses the control and access points of the distributed system 4470 to data and application clients, as well as users of the distributed system, where FIG. 17 is focused on the controls provided to the user of mobility device to grant or revoke access to the collection of types of data by the device at the API and the application levels.

In one embodiment, data streams are real-time data (RTD) collected in relation to the mobility device, such as mobility device diagnostics, information about the mobility of the user while the user is utilizing the device, a user's biometrics (e.g. weight, body temperature, blood pressure, and the like), user's emotional data (e.g. depression, mood, energy levels, etc.), the information about the environment around the device (e.g. temperature, humidity levels, etc.), as well as video, voice, and text communication data collected or traversed through the existing networks.

In one embodiment, real-time data denotes information that is delivered without a delay in the interest of the timeliness of the information provided. Real-time data is often used for navigation or tracking.

As a non-limiting example, dynamic data is different from streaming real-time data because there is no continuous flow of information and updates may come at any time, with periods of inactivity in between. Dynamic data is asynchronously modified as changes to the information become available. Dynamic data can be stored in a relational database while streaming real-time data is fed to a reporting platform, where it might be further filtered or optimized so that the results are displayed in real-time to users.

In one embodiment dynamic data can be information about the patient which is updated intermittently by a physician, a user of the device (patient), or by a technical support team member, such as a patient's age, height, gender, etc.

In one embodiment dynamic data can also be any other previously stored data to which transactional code (e.g. create, remove, update, etc) is expected to be applied at some frequency, as updates to that data become available.

In one embodiment dynamic data can become persistent (static) data if it becomes obsolete. For example, archived data is static data. However, current archived data can have been frequently accessed and updated as a dynamic data before it was superseded by a more current data object.

In one embodiment program or application code is or can be referred to as persistent data, as opposed to static data.

In one embodiment, dynamic and static data, similarly to RTD, is interpreted, stored, or otherwise managed by a computing device utilizing predetermined rules or developed logic, such as application or a software code.

As a non-limiting example of a use case of an application interface and of a data flow, a predefined range of a motion to be completed in n-many sets is a request entered by a physician via the application client interface available to the physician to 'notify' or 'remind' the patient at an appropriate time to complete the required exercises. The patient and the mobility device in turn will interact with the computing device and the application interface on the patient's side to track and perform the requested exercises. This is done in communication with the activity manager of the patient's application interface.

Further non-limiting examples include timely intake of medications, bladder discharge, drinking of fluids, taking meals in desired dosages, etc.

In one embodiment, alerts and similarly defined events warn of a user's ongoing or on-setting hypertension, high or low blood pressure, high or low body temperature, etc.

As a non limiting example, alerts, notifications, and reminders can be implemented visually, audibly, or in combination. This can be done by utilizing user interface elements on the display of the computing device and/or by use of the peripheral augmenting input/output devices controlled by the application and peripherals interface on the patient's side. In one embodiment, illustrated in FIG. 17, mobility device user can grant and revoke access to the user's specific data and access to perform processes on these data.

In one embodiment, also illustrated in FIG. 17, is one possible way to describe at a very high-level the conceptual map of the various data constructs available to the different application layers of the software and also relative to the types of users of the system.

As a non-limiting example, various application interface layers can reveal only the data and controls available to that specific interface layer. Such interface layers can include the 'Technical Support Tools and User Interface (UI)', 'Predictive Analytic Health and Research Tools and UI', 'Developer Tools and UI', 'Physician Tools and UI' and 'Patient or Mobility Device User Tools and UI'.

Patient data can be stored and archived (ex: patient history) as static data collected by the system. However, transactional data also exists within the system and is typically stored in a type of a relational database or across types of relational databases comprising a relational database system. Similarly, types of streaming data are also shown. Different storage and database systems are generally used to store different types of data. Data frequently and asynchronously updated might benefit from a relational database structure. Streaming data is usually stored in a NoSql database, as access is much faster as opposed to transactional database. Static data might be placed in long term storage, as it is history data and not intended for changes or updates.

Additionally, all the data are graphically separated by container structures. These containers depict a type of a logical or a physical separation or their combination between the different data constructs available at any time within the system.

Certain pre-identified streams of data can be separated from other streams by a physical or logical medium in addition to any other securities required to be put in place within the network, such as the limiting software and the application layers, protocols, identity management methods of the system, encrypting of the information, and the like, as illustrated in FIG. 17.

As a non-limiting example, FIG. 17 shows that certain patient (or mobility device user) data, such as patient's motion data, patient biometric data, and patient emotional data can be separated out either logically, or physically, or both from the mobility device related data (device diagnostic data and customer/technical support centric data) and also from data created or supplied in any way by the development team (developer data). In this scope, the data utilized, supplied or developed by the open-platform development teams may additionally be separated out from the primary system and software development.

In one embodiment, such security measures may be set in place by governing legislations in the regions where the data is held, to make sure that any actions performed on these data are monitored, stored, or otherwise collected and made available over a system's networks in accordance with these laws, policies, and regulations of the. Examples of the legislative assemblies known to enact similar laws and the regulations they impose are the U.S. Department of Health & Human Services (HHS) and Food and Drug Administration (FDA) for HIPAA Privacy Rules and HITECH Act and the European Union and the European Commission for the Data Protection Directive (95/46/EC).

In one embodiment, the primary user of the mobility device (or patient) can hold additional authority over certain aspects of the data availability and flows, as identified by arrows in the FIG. 17 pointing at different layers of the architecture of the distributed system.

As a non-limiting example, a user can be provided certain controls to define what personal and health data is allowed to be collected, stored, traversed or otherwise managed within the system, regardless of the physical capabilities of the computing systems alone.

In one embodiment, a schematic representation of 'the cloud' process architecture is illustrated in FIG. 19 and can include any of the following methods and components connected and acting out processes via a configured or built-in or soft-programmed logic and via the communicating physical networks: processes such as data management and exchange, software management systems, media storage, various data stores, load balancing, firewall servers, proxy servers, analytical tools or systems, machine learning and computing clusters, or other such elements all working together as a single system to complete a set of predefined tasks.

A single physical server is a computing device which can serve as a physical or a virtual platform or a combination of these.

Servers can be physical machines or virtual instances created from a predefined template and running on a single physical machine or distributed amongst a set of physical machines. A 'template' in this context provides a way to develop a homogeneous set or a 'cluster' of servers responsible for a specific task or set of tasks within a computing system. Such a cluster usually forms a virtual or a physical cluster. Each of the servers will have a specific computing power, a pre-defined memory size and storage capacity.

A server is an example of a type of computing device which can house a processing unit (CPU), memory and storage within it, and also other types of processing modules, such as a Graphical Processing Unit (GPU).

Servers can run in a virtual private or within a public cloud, i.e. sharing computing power and services, hardware and/or bandwidth with other client systems. Additionally, some parts of a system can have servers running in both types of cloud platforms simultaneously.

In one embodiment a dedicated hardware is AWS 'Dedicated Instances' which are physically isolated at the host hardware level from instances that are not 'Dedicated Instances' and from instances which belong to other AWS accounts.

In one embodiment, a distributed system can include low-latency technology (advanced I/O and hardware design, such as system on chip design, suitable protocol stacks and algorithms, smarter network topologies, better data optimization, etc), multi-region failover strategies, redundancy, scalability, migration strategies, log and data analysis, and securities for data access and management. All of these may be available at least in part to design and customize as an IaaS at a price, or purchased as an existing solution, also at a price, from a 3rd party provider.

In one embodiment, FIG. 16B represents a user interface that can be provided to allow the user to control all the functions of the mobility device, as well as to provide additional connectivity for the user with internet, phone, and social media.

The user interface can be displayed over a console, such as a mounted tablet, mobile device or another computing device. The user interface can then be populated with sensor parameters, context configurations and web-service rules via form fields to create activity profiles as part of the activity manager.

In such an embodiment, the activity manager is preloaded onto the computing device via a download and installation process. An activity manager is thus part of the software or application code provided to interface with the controls of a mobility device. Typically, this interfacing can be achieved via a framework program code. A framework, or an Application Program Interface (API) enables a user to communicate with the controls of mobility device and with any other elements exposed via the API.

An API can expose a set of objects and their libraries to define and describe the components of the mobility device and of the distributed system via elements found on a user interface.

A form field element can be added or removed in some configurations to the user interface, thus providing a type of customization for the user.

Similarly, a value for a provided form field can be updated. Any changes entered here are then synced with the database which communicates with the activity manager.

As non-limiting examples, a mobility device utilizes and/or includes a variety of computer and computing systems, communications devices, networks and/or digital/logic devices for operation. Each may, in turn, be configurable to utilize a suitable computing device, which can be manufactured with, loaded with and/or fetch from some storage device, and then execute, instructions that cause the computing device to perform a method according to aspects of the disclosed subject matter. As example, a suiting computing device may interface with the distributed system in a way that will allow the viewing and the manipulation of data (for example, change device settings such as speed, position, sensitivity etc.). Collectively, the described computer, computing systems, communications devices, networks and/or digital/logic devices can be referred to as a single distributed system.

A user may also communicate through a mobile computing device with doctors, caretakers, family, friends, customer support and any other person, using own proprietary or 3$^{rd}$ party software or applications such as Skype, FaceTime, and the like, but without limitation, and using a video or a telephonic communication as well as via text, instant messaging and the like.

The computing device of the mobility device may also send technical information to the customer support, related to the performance of the mobility device, such as pressure, temperature, battery life, and any other information from the different components of the mobility device, to provide the customer support information about the status of the device components and to enable predictive maintenance in one embodiment.

Various embodiments are described for illustrative purposes as steps of a method, which may be executed on a computing device that is executing software, and illustrated, by way of example only, as a block diagram of a process flow. Such may also be considered as a software 'flow chart'. Such block diagrams and like operational illustrations of a method performed or the operation of a computing device and any combination of blocks in a block diagram, can illustrate, as examples, software program code/instructions that can be provided to the computing device or at least abbreviated statements of the functionalities and operations performed by the computing device in executing the instructions.

Some possible alternate implementation may involve the function, functionalities and operations noted in the blocks of a block diagram occurring out of the order noted in the block diagram, including occurring simultaneously or nearly so, or in another order or not occurring at all. Aspects of the disclosed subject matter may be implemented in parallel or seriatim in hardware, firmware, software or any combination(s) of these, co-located or remotely located, at least in part, from each other, e.g., in arrays or networks of computing devices, over interconnected networks, including the Internet, and the like.

As non-limiting examples, the instructions may be stored on a suitable "machine readable medium" within a computing device or in communication with the computing device, or otherwise accessible to the computing device.

As used in the present application, a machine readable medium is a tangible storage or memory device, and the instructions are stored in a non-transitory way.

At the same time, during operation, the instructions may at some times be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or to a remote server and accessed over a network, or the like. When so stored, the software will constitute a "machine readable medium," that is both tangible and stores the instructions in a non-transitory form.

At a minimum, therefore, the machine readable medium storing instructions for execution on an associated computing device will be "tangible" and "non-transitory" at the time of execution of instructions by a processor of a computing device and when the instructions are being stored for subsequent access by a computing device.

Activity Manager

In one embodiment, a user may also want the activity manager of the mobility device user to track specific items associated with the activity.

As a non-limiting example, the user may want to use specific sensors on the mobility device during an activity of a user and to monitor a variety of physiological factors, such as heart rate.

The sensor IDs or names can be added into the sensor field for the mobility device of a user or for its user. A user can also configure the sensor parameters that he/she wants used during the activity, as front end of data acquisition system. Alternatively, the sensor parameters can be transparent to a user. For example, the parameters can be pre-populated based on success of data collection of prior activity history. This information is then autonomously entered into a sensor parameter field for the mobility device user. In addition to having items tracked (such as heart rate) via the sensors of the mobility device which are monitored during the activity, the user may want to associate a web service with the activity.

In one embodiment, a user may want to associate a weather service with a physiological parameter so that the activity manager of the mobility device user can automatically and dynamically adjust settings on the sensors of the mobility device of that user, determine to track different items, and the like. For example, the activity manager of the mobility device user can additionally monitor the web service to determine if the weather is sunny, cloudy, raining, or the like.

In one embodiment, a user can setup rules that allow a web-service to perform a function based on the context(s). For example, if the weather is rainy, a user can have a rule setup that has a web-service make a reservation at an indoor track.

FIG. 16C may also present a page as part of the application or securely accessed web site for entry of web-service rules into provided fields for the mobility device user. The web service field for the mobility device user allows a user to enter various rules associated with a web-service.

In one embodiment, the user interface's one or more fields may be added to or deleted from the interface. For example, the user interface of the mobility device user can also provide a mechanism to a user for reviewing all entered activities, deleting activities, and the like.

It should also be noted that the user interface can also reside on an information processing system coupled to the monitoring device for the mobility device user.

Additionally, a user interface can reside on another suitable computing device, such as a mobile device or a computer, a console, or a display monitor coupled (FIG. 16) to a suitable processing system or a computing device, for example, on the processing system or the computing device of the mobility device.

The touch-sensitive touch screen provides an input interface and an output interface between the mobility device and its user or designee.

The display controller receives and/or sends electrical signals from/to the touch screen. The touch screen displays visual output to the mobility device user. The visual output may include graphics, text, icons, video, and any combination thereof (collectively termed "graphics").

In some embodiments, some or all of the visual output may correspond to mobility device or designee interface objects, further details of which are described below.

The touch screen may use LCD (liquid crystal display) technology, or LPD (laser powered phosphor display), polymer LED (polyLED) (light emitting polymer display) technology, although other display technologies may be used in other embodiments. The touch screen and the display controller may detect contact and any movement or breaking thereof using any of a plurality of touch sensing technologies now known or later developed, including, but not limited to, capacitive, resistive, infrared, and surface acoustic wave technologies, as well as other proximity sensor arrays or other elements for determining one or more points of contact with a touch screen.

The touch screen may have a resolution in excess of 10 dpi. In an exemplary embodiment, the touch screen has a resolution of approximately 1060 dpi. The mobility device user or designee can make contact with the touch screen using any suitable object or appendage, such as a stylus, a finger, and so forth.

In some embodiments, the mobility device user or designee interface is designed to work primarily with finger-based contacts and gestures, which are much less precise than stylus-based input due to the larger area of contact of a finger on the touch screen.

In some embodiments, the device translates the rough finger-based input into a precise pointer/cursor position or command for performing the actions desired by the mobility device user.

In some embodiments, in addition to the touch screen, the mobile computing device may include a touchpad for activating or deactivating particular functions.

In some embodiments, the touchpad is a touch-sensitive area of the device that, unlike the touch screen, does not display visual output. The touchpad may be a touch-sensitive surface that is separate from the touch screen or an extension of the touch-sensitive surface formed by the touch screen.

In some embodiments, the mobile computing device may include a physical or virtual click wheel as an input control device. A mobility device user can navigate among and interact with one or more graphical objects (henceforth referred to as icons) displayed in the touch screen by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the mobility device user may press down on at least a portion of the click wheel or an associated button. The mobility device user commands and navigation commands can be, as a non-limiting example, via a click wheel processed by an input controller as well as one or more of the modules and/or sets of instructions in memory.

For a virtual click wheel, the click wheel and click wheel controller may be part of the touch screen and the display controller, respectively. For a virtual click wheel, the click wheel may be either an opaque or semitransparent object that appears and disappears on the touch screen display in response to mobility device user interaction.

In some embodiments, a virtual click wheel is displayed on the touch screen of a computing device or a suitable mobile device—coupled to computing device and operated by mobility device user's contact with the touch screen.

The computing device may also include a power system for powering the various components. The power system may include a power management system (FIG. 14A), one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

The computing device may also include one or more sensors, including, but not limited to optical sensors.

An optical sensor can be coupled to an optical sensor controller in I/O subsystem. The optical sensor may include charge-coupled device (CCD) or complementary metal-oxide semiconductor (CMOS) phototransistors. The optical sensor receives light from the environment, projected through one or more lens, and converts the light to data representing an image. In conjunction with an imaging module (also called a camera module), the optical sensor may capture still images or video.

In some embodiments, an optical sensor is located on the back of the computing device, opposite the touch screen display on the front of the device, so that the touch screen display may be used as a viewfinder for either still and/or video image acquisition.

In some embodiments, an optical sensor is located on the front of the device so that the mobility device user image may be obtained for video conferencing while the mobility device user views the other video conference participants on the touch screen display.

In some embodiments, the position of the optical sensor can be changed by the mobility device user (e.g., by rotating the lens and the sensor) so that a single optical sensor may be used along with the touch screen display for both video conferencing and still and/or video image acquisition.

The computing device may also include one or more proximity sensors.

In one embodiment, the proximity sensor is coupled to the peripherals interface. Alternately, the proximity sensor may be coupled to an input controller in the I/O subsystem.

In some embodiments, the proximity sensor turns off and disables the touch screen when the multifunction device is placed near the mobility device user ear (e.g., when the mobility device user is making a phone call).

In some embodiments, the proximity sensor keeps the screen off to prevent unnecessary battery drainage when the device is in a locked state.

In some embodiments, the software components stored in memory may include an operating system, a communication module (or set of instructions), a contact/motion module (or set of instructions), a graphics module (or set of instructions), a text input module (or set of instructions), a Global Positioning System (GPS) module (or set of instructions), and applications (or set of instructions).

The operating system (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module facilitates communication with other devices over one or more external ports and also includes various software components for handling data received by the Network Systems circuitry and/or the external port. The external port (e.g., Universal Serial Bus (USB), FIREWIRE, etc.) is adapted for coupling directly to other devices or indirectly over a network (e.g., the Internet, wireless LAN, etc.).

In some embodiments, the external port is a multi-pin (e.g., 30-pin) connector that is the same as, or similar to and/or compatible with the 30-pin connector used on iPod (trademark of Apple Computer, Inc.) devices.

The contact/motion module may detect contact with the touch screen (in conjunction with the display controller) and other touch sensitive devices (e.g., a touchpad or physical click wheel). The contact/motion module includes various software components for performing various operations related to detection of contact, such as determining if contact has occurred, determining if there is movement of the contact and tracking the movement across the touch screen, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multi-touch"/multiple finger contacts).

In some embodiments, the contact/motion module and the display controller also each detects contact on a touchpad.

In some embodiments, the contact/motion module and the controller each detects contact on a click wheel.

Examples of other applications that may be stored in memory include other word processing applications, JAVA-enabled applications, encryption, digital rights management, voice recognition, and voice replication.

In conjunction with touch screen, display controller, contact module, graphics module, and text input module, a contacts module may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone, video conference, e-mail, or IM; and so forth.

For example, the activity manager of the mobility device user can have software loaded on a personal computer that allows the user to enter the above information or to interact with the activity manager of the mobility device user. The activity manager of the mobility device user can then sync with database of the distributed system to update its data.

In yet another embodiment, a user can enter information directly at an identifier enabled item such as a sensor of/for the mobility device (for the mobility device user if sensor is on the user, for example). For example, a sensor of a mobility device can include a user interface with a calendar. Any information entered here can then be synced with the activity manager. Any configuration parameters such as a heart rate baseline, stride length, and the like are then communicated to the activity manager of the mobility device user.

In one embodiment, information received from a user, for example, via the user interface, can also be provided to a calendar residing within the monitoring device of the mobility device user.

Alternatively, information from the calendar can also be extracted by the activity manager of the mobility device user. For example, if the activity manager of the mobility device user determines that a user has entered a new activity in the calendar, the activity manager of the mobility device user can prompt the user to determine if the user wants the activity manager of the mobility device user to monitor and manage that activity.

Although the calendar is described as residing outside of the activity manager of the mobility device, the activity manager of the mobility device user can include an internal calendar for monitoring lifestyle activities. In other words, the monitoring device of the mobility device user can include a calendar, and the activity manager of the mobility device user can also include an internal calendar used in conjunction with the wireless device calendar (such as of a monitoring device).

In one embodiment, based on the received activity information, the activity manager of the mobility device user creates activity profiles, that are stored in an activity management database. Each activity can be stored within a separate activity profile. A calendar can be provided that calendars events associated with an activity. The activity profile can include various information associated with an activity, such as: a name for an activity, an activity ID, a sensor/device name associated with the activity, an identifier/device IP address; if available, data configuration for the sensor/device and the like.

As a non-limiting example, a mobility device's activity and the web service rules can be associated with a particular web service. For example, a web service A is associated with a certain activity. A web service rule is associated with the web service A that indicates that if the temperature outside is less than 60° F., then reserve an indoor track.

As can be seen, the activity profile then associates an activity to a sensor/device context. The sensor/device context indicates what sensors the mobility device uses, what rules the sensor is associated with, and also the current configurations of these.

In one embodiment, information within the activity profile is independent of a time context or location context associated with an activity.

In one embodiment, the calendar associates a time context with an activity and an optional location context. Therefore, the calendar can also show the location of the activity. Therefore, the activity has a time context and a location context associated with it. The information within the activity profile can be used by the activity manager mobility device user regardless of the time and location contexts.

As a non-limiting example, if the user has defined activity on two different days at two different times and at two different locations, the activity manager mobility device user can still refer to the selected activity profile and use the information included therein for the two instances of the activity. Therefore, the activity manager of the mobility device user monitors both the calendar (which includes also location in this example) and the activity management database.

However, the activity profiles can also include time and location contexts as well. In this example, a separate activity profile is stored in the activity management database for each instance of an activity.

In one embodiment, the activity manager of the mobility device user also includes a context monitoring module.

In one embodiment, the content monitoring module allows the activity manager to determine whether an activity is about to start, has started, or has ended, and either monitor for identifier enabled items and/or initialize sensors mobility device user associated with the activity. For example, the context monitoring module monitors context such as time, location, device, and the like. The context monitoring module can monitor the calendar, GPS, or information entered by the user in order to determine the current time, date and/or location of the wireless device. The activity manager of the mobility device user can therefore compare activity profiles and/or calendar events with the determined time and/or location to determine whether an activity is starting, ending, or the like.

In one embodiment, the (dynamic) activity manager of the mobility device user is communicatively coupled to a GPS module and a display.

The GPS module can be used by the (dynamic) activity manager of the mobility device user to determine the location of the monitoring device of the mobility device user. As a non-limiting example, the display can be used for, among other things, to display data/information, visual alerts to a user.

In one embodiment, the activity manager of the mobility device user manages and monitors identifier enabled items, sensors of the mobility device user, and Network Systems associated with a user activity.

Identifier enabled items can be any item that is coupled to an identifier or other communication tag. The activity manager of the mobility device user monitors identifier enabled items via an identifier enabled item monitor, herein referred to as the "identifier monitor". The identifier monitor, in one embodiment, can be 1) an identifier transceiver embedded with monitoring software or can be 2) a separate monitoring software module coupled to an identifier transceiver.

In one embodiment, the identifier monitor can be configured by the user to automatically start monitoring for items associated with an activity or to continuously monitor for identifier enabled items. For example, when the activity manager determines, based on a time context and/or a location context associated with an activity, that it is time for an activity to start, the activity manager of the mobility device user can begin monitoring for associated identifier enabled items.

As a non-limiting example, if the activity manager of the mobility device user determines that the activity is about to begin, the identifier monitor analyzes the activity profile to determine what items are needed for the activity. The identifier monitor then determines if items such as a heart beat monitor are present. In other words, the identifier monitor determines if an identifier signal from the heartbeat monitor has been detected. The activity manager of the mobility device user can then visually, audibly, and/or tactilely notify the user of the presence or non-presence of the items.

In one embodiment, based on the activity profiles, calendar, and/or an internal clock, the activity manager of the mobility device user can determine whatever the activity may be. For example, a user can have a calendar entry or an activity defined for "leave for work", which begins at 8:00 a.m. Therefore, if the time is 7:30 a.m., the activity manager of the mobility device user can determine that the user has not left for work. In another example, a user can have an activity defined for an activity. The activity manager mobility device user can detect that the user has left the house, entered his/her car or the like either by passing an identifier sensor at a door or via GPS and analyzes the activity profiles accordingly.

As a non-limiting example, the activity manager of the mobility device user, based on activity profiles and/or calendar events, determines that the user is going straight from work after an activity. Therefore, the activity manager of the mobility device user monitors for the items associated with the activity. The activity manager of the mobility device user then notifies the user if these items have been completed.

In one embodiment, in addition to monitoring for associated identifier enabled items when an activity is to begin, the activity manager mobility device user manages sensors of the mobility device user that are associated with the activity. As a non-limiting example, when an activity is about to begin, the activity manager mobility device user analyzes the activity profile associated with the activity and identifies the sensors the mobility device user associated with the activity. If the sensor(s) of the mobility device user have not been initialized, the activity manager of the mobility device user initializes the sensor(s) of the mobility device user using the configuration parameters in the activity profile. For example, the sensors of the mobility device user and the monitoring device of the mobility device user can communicate via a communication manager within the activity manager of the mobility device user. The sensors of the mobility device user and the monitoring device of the mobility device user can communicate using a wireless connection such as BLUETOOTH®, Zigbee, or the like.

In one embodiment, the dynamic activity manager also includes a data fusion module for the mobility device user for performing data fusion with respect to health and information monitored. Other types of data monitored with respect to the current disclosure may also be undergoing data fusion, for example, diagnostic data regarding the health of the mobility device.

In one embodiment, a timing diagram is provided for initializing a sensor of the mobility device based on the activity manager of the mobility device user detecting the start of an activity.

In one embodiment, a user has an activity defined on the user's monitoring device of the mobility device user and wants to invite a friend to the activity:

At time T0 the activity manager of the mobility device user sends an invite associated with the activity to another wireless device. The invite includes the time context, e.g., May 2nd at 2 p.m., and can include an optional location context.

At time T1 the invitee wireless device sends an acceptance message to the initiating (user's) monitoring device of the mobility device user.

At time T2, the activity manager of the mobility device user determines that the time is 2:00 p.m. and queries the activity management database to identify the sensors the mobility device user associated with the activity.

The activity manager of the mobility device user also obtains the IP address of the sensor(s) of the mobility device user. The IP address is used by the communication manager to communicate with the sensor of the mobility device user.

In one example, the sensors of the mobility device user associated with the activity are a sensor on the user. A different type of sensor can also be utilized for another parameter.

In one embodiment, at time T3 the activity manager of the mobility device user pings the sensors of the mobility device user to determine if they have been initialized. If the sensors mobility device user have not been initialized, the activity manager of the mobility device user identifies the configurations parameters of the sensors from the activity profile and initializes the sensors of the mobility device user accordingly. The sensors of the mobility device user, at time T4, send a ready response to the activity manager of the mobility device user. At time T5 the activity manager of mobility device user begins collecting data from the sensors of the mobility device user. The activity manager of the mobility device user, at time T6, determines that the activity has completed. At time T7, the activity manager of the mobility device user displays (to this point) collected data from the sensors of the mobility device user to the user via the user interface (where the activity manager does not have to wait for the activity to finish to start displaying data from sensors).

In one embodiment, a user can configure the activity manager of the mobility device user to only collect specific data from a sensor of the mobility device user or not all data. Also, the activity manager of the mobility device user does not have to communicate with a sensor of the mobility device user during an activity. For example, a user may have forgotten the monitoring device at her house.

In one embodiment, the activity manager of the mobility device user determines that an activity is starting, but sensors of the mobility device user are not in the vicinity. When sensors of the mobility device user come back into range with the monitoring device of the mobility device user, the activity manager of the mobility device user queries the sensor of the mobility device user for the data collected during the activity. In one example, the sensors of the mobility device user collect data continuously, and in another example, the sensor of the mobility device user only collects data during scheduled activities. For example, a user's watch may have a biometric sensor that collects data throughout the day. However, the user may only be concerned with plotting data during an activity.

In the above embodiments, the sensors can include memory for storing data, such as in an MCU (Microcontroller Unit).

In one embodiment, the activity manager of the mobility device user can also monitor and manage Network Systems associated with an activity. For example, a user can define rules associated with Network Systems that are to be applied to the activity profile of the mobility device user with respect to an activity. One example is where a user subscribes to a weather service. The user can define a rule that states if the weather is rainy during the time period associated with an activity, then delay any monitoring or managing for that activity for 1 hour. Another rule can state to delay any managing or monitoring until a user prompt is received. The activity manager of the mobility device user can query Network System at the start or prior to an activity starting to obtain the required information. Similarly, a user of the mobility device can specify a type of Network Systems circuitry to use for any particular activity via activity profile and rules. (WiFi, Bluetooth, Cellular Network Provider, etc.)

As used herein the term "engine" refers to software, firmware, hardware, or other component that can be used to effectuate a purpose. The engine will typically include software instructions that are stored in non-volatile memory (also referred to as secondary memory) and a processor with instructions to execute the software. When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term "computer" is a general purpose device that can be programmed to carry out a finite set of arithmetic or logical operations. Since a sequence of operations can be readily changed, the computer can solve more than one kind of problem. A computer can include at least one processing element, typically a central processing unit (CPU), and some form of memory. The processing element carries out arithmetic and logic operations, and a sequencing and control unit can change the order of operations based on stored information. Peripheral devices allow information to be retrieved from an external source, and the result of operations saved and retrieved. A computer also includes a graphic display medium.

As used herein, the term "Internet" is a global system of interconnected computer networks that use the standard Network Systems protocol suite (TCP/IP) to serve billions of users worldwide. It is a network of networks that consists of millions of private, public, academic, business, and government networks, of local to global scope, that are linked by a broad array of electronic, wireless and optical networking technologies. The Internet carries an extensive range of information resources and services, such as the inter-linked hypertext documents of the World Wide Web (WWW) and the infrastructure to support email. The communications infrastructure of the Internet consists of its hardware components and of system of software, firmware and network layers that control various aspects of the architecture.

As used herein, the term "Extranet" is a computer network that allows controlled access from the outside. An Extranet can be an extension of an organization's Intranet that is extended to users outside the organization in isolation from all other Internet users. An Extranet can be an Intranet mapped onto the public Internet or some other transmission system not accessible to the general public, but managed by more than one company's administrator(s). Examples of extranet-style networks include but are not limited to:

As used herein, the term "Intranet" is a network that is owned by a single organization that controls its security policies and network management. Examples of Intranets include but are not limited to:

A local area network (LAN).

A Wide-area network (WAN) that is comprised of a LAN that extends usage to remote employees with dial-up access A WAN that is comprised of interconnected LANs using dedicated communication lines LANs or WANs belonging to multiple organizations and interconnected and accessed using remote dial-up LANs or WANs belonging to multiple organizations and interconnected and accessed using dedicated lines A Virtual private network (VPN) that is comprised of a LAN or WAN that extends usage to remote employees or networks using special "tunneling" software that creates a secure, usually encrypted connection over public lines, sometimes via an Internet Service Provider (ISP).

For purposes of the present disclosure, the Internet, Extranets and Intranets collectively are referred to as ("Network Systems").

As used herein "Cloud Application" refers to cloud application services or "software as a service" (SaaS) which deliver software over the Network Systems eliminating the need to install and run the application on a device.

As used herein "Cloud Platform" refers to a cloud platform services or "platform as a service" (PaaS) which deliver a computing platform and/or solution stack as a service, and facilitates the deployment of applications without the cost and complexity of obtaining and managing the underlying hardware and software layers.

As used herein "Cloud System" refers to cloud infrastructure services or "infrastructure as a service" (IAAS) which deliver computer infrastructure as a service with raw block storage and networking.

As used herein "Server" refers to server layers that consist of computer hardware, firmware and/or software products specifically designed for the delivery of cloud services.

As used herein, the term "database" is any means for storing data, whether centralized or distributed, relational or otherwise.

As used herein, the term "mobility device user monitoring" includes: (i) cardiac monitoring, which generally refers to continuous electrocardiography with assessment of the user's condition relative to their cardiac rhythm. A small monitor worn by an ambulatory user for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves $CO_2$ measurements, referred to as EtCO2 or end-tidal carbon dioxide concentration. The respiratory rate monitored as such is called AWRR or airway respiratory rate. (iv) Respiratory rate monitoring through a thoracic transducer belt, an ECG channel or via capnography, (v) Neurological monitoring, such as of intracranial pressure, (vi) body weight monitoring. Special user monitors can incorporate the monitoring of brain waves electroencephalography, gas anesthetic concentrations, bispectral index (BIS), and the like, (vii) blood glucose monitoring using glucose sensors, (viii) childbirth monitoring with sensors that monitor various aspects of childbirth, (ix) body temperature monitoring which in one embodiment is through an adhesive pad containing a thermoelectric transducer, (x) stress monitoring that can utilize sensors to provide warnings when stress levels signs are rising before a human can notice it and provide alerts and suggestions, (xi) epilepsy monitoring, (xii) toxicity monitoring, (xiii) general lifestyle parameters, (xiv) sleep, including but not limited to: sleep patterns, type of sleep, sleep disorders, movement during sleep, waking up, falling asleep, problems with sleep, habits during, before and after sleep, time of sleep, length sleep in terms of the amount of time for each sleep, body activities during sleep, brain patterns during sleep and the like (xv) body gesture, movement and motion (xvi) body habits, (xvii) and the like.

As used herein a "mobile device" includes, but is not limited to, cell phones, such as Apple's iPhone®, portable electronic devices, such as Apple's iPod Touch® or Apple's iPad®, mobile devices based on Google's Android® operating system, and any other portable electronic device that includes software, firmware, hardware, or a combination thereof that is capable of at least receiving a wireless signal, decoding and encoding, if needed, and exchanging information with a server. Typical components of a mobile computing device may include, but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device. A mobile device can also include a fob and its equivalents to grant access to the user.

Example Embodiments

The following are examples of further embodiments. Examples may include subject matter such as a mobility device, a seat system, a robotic elevation system, or a drive system.

Example 1 is a robotic elevation system, including a controller to receive an input signal indicating a desired motion of the robotic elevation system and to provide one or more output signals to elements of the robotic elevation system to effectuate the desired motion, an end effector disposed at a distal end of the robotic elevation system, a linear actuator to receive an output signal of the one or more output signals and move in a linear direction in accordance with the desired motion, a rotator connected to a base at a proximal end of the robotic elevation system, the linear rotator to receive an output signal of the one or more output signals and pivot the linear actuator relative to the base, a first joint coupling the end effector and the linear actuator, the first joint to receive an output signal of the one or more output signals and move the end effector relative to the linear actuator based on the desired motion, and a second joint coupling the linear actuator and the rotator, the second joint to receive an output signal of the one or more output signals and move the linear actuator relative to the rotator based on the desired motion.

Example 2 includes the robotic elevation system of example 1, further comprising a gas spring configured to counter balance a weight of a user.

Example 3 includes the robotic elevation system of example 1, wherein the end effector includes at least one sensor.

Example 4 includes the robotic elevation system of example 3, wherein the controller determines the output signal based on the received input signal and a signal from the at least one sensor.

Example 5 includes the robotic elevation system of example 1, wherein the robotic elevation system is connected to a mobility device.

Example 6 includes the robotic elevation system of example 1, wherein the end effector is connected to a seat of the mobility device.

Example 7 includes the robotic elevation system of example 6, wherein the end effector includes at least one load sensor.

Example 8 includes the robotic elevation system of example 7, wherein the controller determines an output signal based on the input signal and a signal from the at least one load sensor.

Example 9 includes the robotic elevation system of example 5, wherein the rotator is connected to a base system of the mobility device.

Example 10 includes the robotic elevation system of example 1, wherein the controller is configured to maintain a center of gravity of the mobility device above a base system of the mobility device when determining the one or more output signals.

Example 11 includes the robotic elevation system of example 1, wherein the controller is configured to maintain a center of gravity of the mobility device relative to the ground when determining the one or more output signals.

Example 12 includes the robotic elevation system of example 1, further including a first angle measuring sensor configured to determine a position of the first joint, a linear measuring sensor configured to determine a position of the linear actuator, and a second angle measuring sensor configured to determine a position of the second joint.

Example 13 includes an end effector located at a distal end of the robotic elevation system, a linear actuator configured to move in a linear direction, a rotator located at a proximate end of the robotic elevation system, the linear rotator configured to pivot the linear actuator relative to the base, a first joint connected to the end effector and the linear actuator, the first joint configured to move the end effector relative to the linear actuator, and a second joint connected to the linear actuator and the rotator, the second joint configured to move the linear actuator relative to the rotator.

Example 14 includes the robotic elevation system of example 13,
further including a gas spring configured to counter balance a weight of a user.

Example 15 includes the robotic elevation system of example 13, wherein the end effector includes at least one sensor.

Example 16 includes the robotic elevation system of example 13, wherein the robotic elevation system is connected to a mobility device.

Example 17 includes the robotic elevation system of example 16, wherein the end effector is connected to a seat of the mobility device.

Example 18 includes the robotic elevation system of example 16, wherein the rotator is connected to a base system of the mobility device.

Example 19 includes the robotic elevation system of claim 16, wherein the rotator pivots the linear actuator about an axis that is parallel to a rear center omnidirectional wheel of the base system.

Example 20 includes the robotic elevation system of example 13, further including a first angle measuring sensor configured to determine a position of the first joint, a second angle measuring sensor configured to determine a position of the second joint, a third angle measuring sensor configured to determine a position of the rotator, and a linear measuring sensor configured to determine a position of the linear actuator.

Example 21 includes a three-wheel drive system for a device, including a base including a front portion and a rear portion, a first omnidirectional wheel mounted at a first side of the front portion of the base to rotate about a first axis, a second omnidirectional wheel mounted at a second side of the front portion of the base to rotate about the first axis, and a third omnidirectional wheel mounted at the rear portion of the base on a second axis oriented perpendicular to the first axis.

Example 22 includes the three-wheel drive system of example 21, wherein the first omnidirectional wheel and the second omnidirectional wheel are each a Mecanum wheel.

Example 23 includes the three-wheel drive system of example 21, wherein the third omnidirectional wheel is a plurality of stacked omnidirectional wheels.

Example 24 includes the three-wheel drive system of example 21, further including a first motor connected to the first omnidirectional wheel, a second motor connected to the second omnidirectional wheel, and a third motor connected to the third omnidirectional wheel.

Example 25 includes the three-wheel drive system of example 24, wherein each motor of the first omnidirectional wheel, the second omnidirectional wheel, and the third omnidirectional wheel receives a control signal from a controller to drive the motors in a coordinated manner to move the device in any given direction.

Example 26 includes the three-wheel drive system of example 25, wherein the device rotates, swerves, or weaves from side-to-side while moving in a forward, backward, lateral or diagonal motion.

Example 27 includes the three-wheel drive system of 24, wherein each of the first motor, the second motor, and the third motor is connected to the corresponding omnidirectional wheel through a damping element.

Example 28 includes the three-wheel drive system of example 21, further comprising a first suspension spring element connected to the first omnidirectional wheel and a second suspension spring element connected to the second omnidirectional wheel.

Example 29 includes the three-wheel drive system of example 21, wherein the device is a mobility device.

Example 30 includes the three-wheel drive system of example 21, wherein the base is connected to a robotic elevation system.

Example 31 includes the three-wheel drive system of example 21, further comprising an axel and the first omnidirectional wheel and the second omnidirectional wheel are mounted on the axel.

Example 32 includes a three-wheel drive system for a device, including a control system configured to output a first control signal, a second control signal, and a third control signal, a base including a front portion and a rear portion, a first omnidirectional wheel mounted at a first side of the front portion of the base to rotate about a first axis, a first motor connected to the first omnidirectional wheel, the first motor configured to drive the first omnidirectional wheel based on the first control signal, a second omnidirectional wheel mounted at a second side of the front portion of the base to rotate about the first axis, a second motor connected to the second omnidirectional wheel, the second motor configured to drive the second omnidirectional wheel based on the second control signal, a third omnidirectional wheel mounted on a rear portion of the base on a second axis perpendicular to the first axis, and a third motor connected to the third omnidirectional wheel, the third motor configured to drive the third omnidirectional wheel based on the third control signal.

Example 33 includes the three-wheel drive system of f example 32, wherein the first omnidirectional wheel and the second omnidirectional wheel are each a Mecanum wheel.

Example 34 includes the three-wheel drive system of example 32, wherein the device rotates, swerves, or weaves from side-to-side while moving in a forward, backward, lateral or diagonal motion.

Example 35 includes the three-wheel drive system of example 32, wherein each of the first motor, the second motor, and the third motor is connected to the corresponding omnidirectional wheel through a damping element.

Example 36 includes the three-wheel drive system of example 32, further comprising a first suspension spring element connected to the first omnidirectional wheel and a second suspension spring element connected to the second omnidirectional wheel.

Example 37 includes the three-wheel drive system of example 32, wherein the device is a mobility device.

Example 38 includes the three-wheel drive system of example 32, wherein the base is connected to a robotic elevation system.

Example 39 includes the three-wheel drive system of example 32, further comprising an axel and the first omnidirectional wheel and the second omnidirectional wheel are mounted on the axel.

Example 40 includes the three-wheel drive system of claim 32, wherein the third omnidirectional wheel is a plurality of stacked omnidirectional wheels.

Example 41 includes a hybrid control system mobility device, including a control system to receive input indicating a desired motion for the mobility device, the control system including a manual control system and an electronic control system, an adjustable seat including a linear actuator that is coupled to the control system and that drives the adjustable seat in a vertical direction based on the input received at the control system, and a drive system coupled to the control system and including a first omni-directional wheel, a second omni-directional wheel, and a third wheel, the drive system to move the first omni-directional wheel, the second omni-directional wheel and the third wheel based on the input received at the control system.

Example 42 includes the hybrid control system mobility device of example 41, wherein the manual control system includes two handle bars, each handle bar movable in a forward and backward direction to indicate the desired motion.

Example 43 includes the hybrid control system mobility device of example 42, wherein the two handle bars each include a handle and a handbrake.

Example 44 includes the hybrid control system mobility device of example 41, wherein the control system includes an electronic control system including a user control to receive the desired motion.

Example 45 includes the hybrid control system mobility device of example 44, wherein the user control is a joystick.

Example 46 includes the hybrid control system mobility device of example 41, wherein the first omnidirectional wheel and the second omnidirectional wheel are Mecanum wheels.

Example 47 includes the hybrid control system mobility device of example 41, wherein the first omnidirectional wheel and the second omnidirectional wheel are on a first axis, and the third wheel is on a second axis parallel to the first axis.

Example 48 includes the hybrid control system mobility device of example 41, wherein the linear actuator is a rear linear actuator and the adjustable seat further includes a front linear actuator and a tilt linear actuator.

Example 49 includes the hybrid control system mobility device of example 48, wherein the rear linear actuator and the front linear actuator each extend and compress in a coordinated manner to position the mobility device in a lowered position, a raised position, or any position in between the lowered position and the raised position.

Example 50 includes the hybrid control system mobility device of example 48, wherein the tilt linear actuator tilts the adjustable seat in a forward and backward motion relative to the front linear actuator.

Example 51 includes a mobility device, including a base, a first omnidirectional wheel mounted at a first side of a forward portion of the base to rotate about a first axis, a second omnidirectional wheel mounted at a second side of the forward portion of the base to rotate about the first axis, a third wheel mounted at a rearward portion of the base to rotate about a second axis, a drive system to move at least one of the first omnidirectional wheel, the second omnidirectional wheel, and the third wheel according to input received indicating a desired motion of the mobility device, a seat for a user of the mobility device, and a linear actuator coupling the seat to the base to drive the adjustable seat in a vertical direction according to the input received indicating the desired motion of the mobility device.

Example 52 includes the mobility device of example 51, further comprising a hybrid control system to receive the input indicating a desired motion for the mobility device, the hybrid control system including a manual control system and an electronic control system.

Example 53 includes the mobility device of example 52, wherein the manual control system including two handle bars, each handle bar movable in a forward and backward direction to provide the input indicating the desired motion of the mobility device.

Example 54 includes the mobility device of example 52, wherein the electronic control system includes a joystick, an underarm steering mechanism, or a user interface to receive the input indicating the desired motion of the mobility device.

Example 55 includes the mobility device of example 51, wherein the first omnidirectional wheel and the second omnidirectional wheel are Mecanum wheels.

Example 56 includes the robotic elevation system of example 51, wherein the first omnidirectional wheel and the second omnidirectional wheel are on a first axis, and the third wheel is on a second axis parallel to the first axis.

Example 57 includes the mobility device of example 51, wherein the linear actuator is a rear linear actuator and the adjustable seat further includes a front linear actuator and a tilt linear actuator.

Example 58 includes the mobility device of example 57, wherein in a lowered position, the rear linear actuator is compressed and the front linear actuator is extended, and when in a raised position, the rear linear actuator is extended and the front linear actuator is compressed.

Example 59 includes a method of operating a mobility device, including receiving a manual input at a manual control system from a user for a desired motion of the mobility device, receiving an input from a user interface of an electronic control system for a desired motion of the mobility device, driving an adjustable seat in a vertical direction based on the input from the user interface, and moving a first omnidirectional wheel, a second omnidirectional wheel, and a third wheel of the mobility device based on the manual input or the input from the user interface.

Example 60 includes method of operating a mobility device of example 59, further comprising tilting the adjustable seat in a forward and backward motion based on the input from the user interface.

Example 61 includes an adjustable seat for a mobility device, including a main seat body, an adjustable back support pivotably attached to the main seat body, wherein the adjustable back support pivots about a first axis to transition between a position perpendicular to the main seat body and a position planar to the main seat body, and two adjustable side arms, each side arm connected to an opposite side of the adjustable back support and each side arm pivotable about a second axis, perpendicular to the first axis, to transition from a position in a plane parallel to the main seat body and position in a plane perpendicular to the main seat body.

Example 62 includes the adjustable seat of example 61, wherein the main seat body is flat.

Example 63 includes the adjustable seat of example 61, wherein the main seat body conforms to a user.

Example 64 includes the adjustable seat of example 61, wherein each of the two adjustable side arms move laterally along a third axis perpendicular to the first axis and the second axis.

Example 65 includes the adjustable seat of example 61, further including a frontal arch connected to the main seat body, the frontal arch including an aperture.

Example 66 includes the adjustable seat of example 65, wherein the frontal arch pivots about a third axis parallel to the first axis to be positioned perpendicular to the main seat body or parallel to the main seat body.

Example 67 includes the adjustable seat of example 61, wherein the back support includes at least one roller.

Example 68 includes the adjustable seat of example 61, wherein the back support includes at least one aperture.

Example 69 includes the adjustable seat of example 68, wherein the back support includes two apertures and further includes a strap through the two apertures which secures around a user.

Example 70 includes the adjustable seat of example 61, further including a front linear actuator, a rear linear actuator adjacent the front linear actuator, and a tilt actuator connected to the front linear actuator.

Example 71 includes adjustable seat of example 70, wherein the tilt actuator tilts the adjustable seat relative to the front linear actuator.

Example 72 includes the adjustable seat of example 61, further including at least two seat wings, each seat wing located on an opposite side of the main seat body, each seat wing pivotable about a third axis perpendicular to both the first axis and the second axis.

Example 73 includes an adjustable seat for a mobility device, including a main seat body, an adjustable back support pivotably attached to the main seat body, wherein the adjustable back support pivots about a first axis to be positioned perpendicular to the main seat body or planar to the main seat body, a frontal arch support pivotably connected to the main seat body about a second axis parallel to the first axis, the frontal arch support including an aperture, at least two seat wings, each seat wing located on an opposite side of the main seat body, each seat wing pivotable about a third axis perpendicular to the first axis and the second axis.

Example 74 includes adjustable seat of example 73, further comprising two adjustable side arms, each side arm connected to an opposite side of the adjustable back support and each side arm pivotable about a fourth axis, perpendicular to the first axis, to be positioned in a plane parallel to the main seat body or in a plane perpendicular to the main seat body.

Example 75 includes adjustable seat of example 73, wherein each of the two adjustable side arms move laterally along the a fifth axis perpendicular to the fourth axis.

Example 76 includes the adjustable seat of example 73, wherein the main seat body conforms to a user.

Example 77 includes the adjustable seat of example 73, wherein the frontal arch pivots about a third axis parallel to the first axis to be positioned perpendicular to the main seat body or parallel to the main seat body.

Example 78 includes the adjustable seat of example 73, wherein the back support includes at least one roller and at least one aperture.

Example 79 includes the adjustable seat of example 73, further including a front linear actuator, a rear linear actuator adjacent the front linear actuator, and a tilt actuator connected to the front linear actuator.

Example 80 includes adjustable seat of example 79, wherein the tilt actuator tilts the adjustable seat relative to the front linear actuator.

It will be obvious to those having skill in the art that many changes may be made to the details of the above-described embodiments without departing from the underlying principles of the disclosure. The scope of the present disclosure should, therefore, be determined only by the following claims.

The invention claimed is:

1. A robotic elevation system, comprising:
a controller configured to receive an input signal indicating a desired motion of the robotic elevation system and further configured to provide one or more output signals to elements of the robotic elevation system to effectuate the desired motion, wherein the desired motion includes movement of the robotic elevation system relative to one or a combination of a first axis, a second axis, and a third axis;
a robotic arm in operable communication with the controller, the robotic arm including:
an end effector disposed at a distal end of the robotic arm;
a linear actuator configured to receive a first output signal of the one or more output signals and to move in a linear direction based on the first output signal in accordance with the desired motion;

a rotator coupled to a base at a proximal end of the robotic arm, the rotator configured to receive a second output signal of the one or more output signals and to pivot the linear actuator relative to the base based on the second output signal;

a first joint coupling the end effector and the linear actuator, the first joint configured to receive a third output signal of the one or more output signals and to move the end effector relative to the linear actuator based on the third output signal in accordance with the desired motion; and a second joint coupling the linear actuator and the rotator, the second joint configured to receive a fourth output signal of the one or more output signals and to move the linear actuator relative to the rotator based on the fourth output signal in accordance with the desired motion, a linear measuring sensor in operable communication with the linear actuator and configured to determine a position of the linear actuator;

a first angle measuring sensor in operable communication with the first joint and configured to determine a position of the first joint; and a second angle measuring sensor in operable communication with the second joint and configured to determine a position of the second joint.

2. The robotic elevation system of claim 1, further comprising a gas spring configured to counter balance a weight of a user.

3. The robotic elevation system of claim 1, wherein the end effector includes at least one sensor.

4. The robotic elevation system of claim 3, wherein the controller determines the one or more output signals based on the received input signal and a signal from the at least one sensor of the end effector.

5. The robotic elevation system of claim 1, wherein the robotic elevation system is coupled to a mobility device.

6. The robotic elevation system of claim 5, wherein the mobility device includes a seat, and wherein the end effector is coupled to the seat of the mobility device.

7. The robotic elevation system of claim 6, wherein the end effector includes at least one load sensor.

8. The robotic elevation system of claim 7, wherein the controller determines the one or more output signals based on the received input signal and a signal from the at least one load sensor of the end effector.

9. The robotic elevation system of claim 5, wherein the rotator is coupled to a base system of the mobility device.

10. The robotic elevation system of claim 5, wherein the controller is configured to determine a center of gravity of the mobility device and to maintain the center of gravity of the mobility device above a base system of the mobility device when determining the one or more output signals.

11. The robotic elevation system of claim 6, wherein the controller is configured to determine a center of gravity of the mobility device and to maintain the center of gravity of the mobility device relative to the ground when determining the one or more output signals.

12. A robotic elevation system, comprising:

an end effector located at a distal end of the robotic elevation system;

a linear actuator configured to move in a linear direction;

a linear measuring sensor configured to determine a position of the linear actuator;

a rotator located at a proximal end of the robotic elevation system, the rotator configured to pivot the linear actuator relative to the base;

a first angle measuring sensor configured to determine a position of the rotator;

a first joint coupled to the end effector and the linear actuator, the first joint configured to move the end effector relative to the linear actuator;

a second angle measuring sensor configured to determine a position of the first joint;

a second joint coupled to the linear actuator and the rotator, the second joint configured to move the linear actuator relative to the rotator; and a third angle measuring sensor configured to determine a position of the second joint, wherein the end effector, linear actuator, and rotator cooperate to coordinate movement of the robotic elevation system relative to one or a combination of a first axis, a second axis, and a third axis.

13. The robotic elevation system of claim 12, further comprising a gas spring configured to counter balance a weight of a user.

14. The robotic elevation system of claim 12, wherein the end effector includes at least one sensor.

15. The robotic elevation system of claim 12, wherein the robotic elevation system is coupled to a mobility device.

16. The robotic elevation system of claim 15, wherein the mobility device includes a seat, and wherein the end effector is coupled to the seat of the mobility device.

17. The robotic elevation system of claim 15, wherein the rotator is coupled to a base system of the mobility device.

18. The robotic elevation system of claim 15, wherein the mobility device includes a base system having an omnidirectional wheel, and wherein the rotator pivots the linear actuator about an axis that is parallel to the omnidirectional wheel of the base system.

* * * * *